United States Patent [19]

Noguchi et al.

[11] 4,263,039

[45] Apr. 21, 1981

[54] M-PHENOXYBENZAMIDE DERIVATIVES

[75] Inventors: Hiroshi Noguchi, Sonehigashi; Shunichi Hashimoto, Takarazuka; Shigeyoshi Kitamura, Sonehigashi; Takashi Matsuo, Saitama; Akihiko Mine, Kawanishi; Katsuzo Kamoshita, Sonehigashi, all of Japan

[73] Assignee: Sumitomo Chemical Company, Limited, Osaka, Japan

[21] Appl. No.: 44,249

[22] Filed: May 31, 1979

Related U.S. Application Data

[62] Division of Ser. No. 792,221, Apr. 29, 1977, Pat. No. 4,173,464.

[30] Foreign Application Priority Data

| May 7, 1976 | [JP] | Japan | 51/52430 |
| May 13, 1976 | [JP] | Japan | 51/54989 |
| Oct. 6, 1976 | [JP] | Japan | 51/120754 |
| Dec. 28, 1976 | [JP] | Japan | 51/160388 |

[51] Int. Cl.³ .................. A01N 43/36; C07D 207/06
[52] U.S. Cl. .......................................... 71/95; 71/88; 71/94; 71/118; 260/239 BF; 260/239 E; 260/326.5 E; 260/465 D; 544/176; 546/226; 564/171; 564/174
[58] Field of Search ............ 260/326.5 E; 71/95

[56] References Cited

U.S. PATENT DOCUMENTS

| 3,449,419 | 6/1969 | Wechter | 260/326.5 E |
| 3,784,635 | 1/1974 | Theissen | 260/471 R |
| 4,090,865 | 5/1978 | Baker | 71/95 |
| 4,191,554 | 3/1980 | Gregory | 260/326.5 E |
| 4,208,205 | 6/1980 | Fawsi | 71/95 |

FOREIGN PATENT DOCUMENTS 51-29226  3/1976  Japan ............ 71/95

OTHER PUBLICATIONS

Chem. Abstracts 75: 75161k(1971), A. Baruffini et al.

Primary Examiner—Donald G. Daus
Assistant Examiner—M. C. Eakin
Attorney, Agent, or Firm—Birch, Stewart, Kolasch and Birch

[57] ABSTRACT

A herbicidal composition which comprises as an active ingredient a m-phenoxybenzamide compound of the formula:

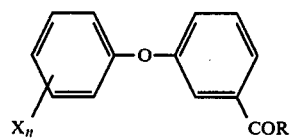

wherein X, which may be the same or different, is a halogen atom or a lower alkyl or lower alkoxy group, n is zero or an integer of 1 to 5 and R is a group of the formula:

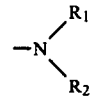

(in which $R_1$ *is a hydrogen atom or a lower alkyl or lower alkenyl group and* $R_2$ is a lower alkyl, lower alkenyl, lower alkynyl, lower alkoxy, lower cycloalkyl, lower haloalkyl, lower alkoxy-substituted lower alkyl, lower cyanoalkyl, lower alkylamino-substituted lower alkyl or benzyl group) or an ethylenimino, pyrrolidino, dimethylpyrrolidino, piperidino, methylpiperidino, hexamethylenimino, morpholino or dimethylmorpholino group.

9 Claims, No Drawings

M-PHENOXYBENZAMIDE DERIVATIVES

This application is a divisional of copending application Ser. No. 792,221, filed on Apr. 29, 1977, now U.S. Pat. No. 4,173,464.

The present invention relates to m-phenoxybenzamide derivatives, and their production and use. More particularly, it relates to (1) a herbicidal composition which comprises as an active ingredient a m-phenoxybenzamide compound of the formula (I):

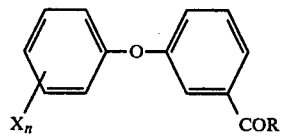

wherein X, which may be the same or different, is a halogen atom or a lower alkyl or lower alkoxy group, n is zero or an integer of 1 to 5 and R is a group of the formula:

(in which $R_1$ is a hydrogen atom or a lower alkyl or lower alkenyl group and $R_2$ is a lower alkyl, lower alkenyl, lower alkynyl, lower alkoxy, lower cycloalkyl, lower haloalkyl, lower alkoxy-substituted lower alkyl, lower cyanoalkyl, lower alkylamino-substituted lower alkyl or benzyl group) or an ethylenimino, pyrrolidino, dimethylpyrrolidino, piperidino, methylpiperidino, hexamethylenimino, morpholino or dimethylmorpholino group; (2) a new m-phenoxybenzamide compound of the formula (II):

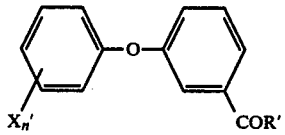

wherein X is as defined above, n' is an integer of 1 to 5 and R' is a group of the formula:

(in which $R_1'$ is a hydrogen atom or a lower alkyl group and $R_2'$ is a lower alkyl, lower alkenyl, lower alkynyl, lower cycloalkyl, lower haloalkyl, lower alkoxy-substituted lower alkyl, lower cyanoalkyl or benzyl group), a pyrrolidino, methylpiperidino, morpholino or dimethylmorpholino group; (3) a process for preparing the m-phenoxybenzamide compound of the formula (II) which comprises reacting a m-phenoxybenzoic acid of the formula (III):

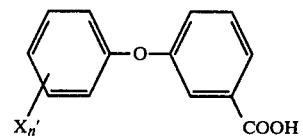

wherein X and n' are each as defined above, or its reactive derivative (e.g. acid halides, acid azides, acid anhydrides, esters) with an amine of the formula (IV):

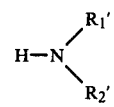

wherein $R_1'$ and $R_2'$ are each as defined above, or pyrrolidine, methylpiperidine, morpholine or dimethylmorpholine; (4) a process for preparing the m-phenoxybenzamide compound of the formula (II) which comprises reacting a m-halobenzamide of the formula (V):

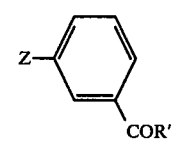

wherein Z is a halogen atom and R' is as defined above with a phenol of the formula (VI):

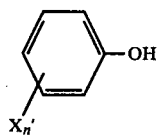

wherein X and n' are each as defined above; and (5) a process for preparing the m-phenoxybenzamide compound of the formula (II) which comprises reacting a m-hydroxybenzamide of the formula (VII):

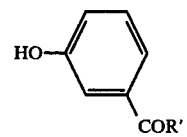

wherein R' is as defined above with a halobenzene of the formula (VIII):

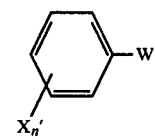

wherein W is a halogen atom and X and n' are each as defined above.

As the result of an extensive study seeking herbicidally active substances having a wide herbicidal spectrum including perennial weeds, it has now been found that the m-phenoxybenzamide compounds of the formula (I) have a strong herbicidal activity. Most of the m-phenoxybenzamide compounds (I) are novel, and the rest are known in the literatures (Japanese Patent Publication (unexamined) Nos. 61443/1973 and 61405/1973) which however disclose the preparation process alone of the compounds and no herbicidal activity thereof. Some of the o- or p-phenoxybenzamide compounds are also known in the literatures (Zh. Org. Khim., 1968, 4 (10), 1836; J. Karnatak Univ., 2.33 (1957); J. Karnatak Univ., 3.63 (1958)), but it is not known that these compounds have a herbicidal activity and, in fact, they have little or no herbicidal activity.

The m-phenoxybenzamide compounds (I) have a strong herbicidal activity not only on the weeds in upland fields but also on the weeds in paddy fields. The former weeds include grassy weeds such as barnyard grass (*Echinochloa crus-galli*), large crabgrass (*Digitaria sanguinalis*), green foxtail (*Setaria viridis*), water foxtail (*Alopecurus aequalis*) and the like, and broad-leaved weeds such as nutsedge sp. (*Cyperus difformis*), redroot pigweed (*Amaranthus retroflexus*), common lambsquarter (*Chenopodium album*), common purslane (*Portulaca oleracea*), chickweed (*Stellaria media*) and the like. The latter weeds include annual weeds such as barnyard grass (*Echinochloa crus-galli*), monochoria (*Monochoria viaginalis* Presl.) toothcup (*Rotala indica* Koehne), *Dopatrium junceum* and the like, and perennial weeds such as *Cyperus serotinus*, arrowhead sp. (*Sagittaria pygmaea*), hardstem bulrush (*Scirpus juncoides*), *Eleocharis kuroguwai*, slender spikerush (*Eleocharis acicularis*) and the like.

The m-phenoxybenzamide compounds (I) kill these weeds mainly by chlorosis and have a wide herbicidal spectrum. They exert a characteristically strong herbicidal activity on the perennial weeds in paddy fields, which are difficult to control with conventional herbicides for paddy fields and besides have recently increased greatly and become a serious problem. Both by pre-emergence and foliar treatment, they exert a strong activity on the perennial weeds as well as the annual weeds. Further, they are superior in a long persistence of efficiency and in a very large selectivity between rice plants and barnyard grass which makes it possible to use them in rice fields without any injury.

The m-phenoxybenzamide compounds (I) also have strong herbicidal activity on the main weeds in upland fields and the activity is exhibited by both pre-emergence and post-emergence treatments. Nevertheless, they have no phytotoxicity to important crops such as rice plant, soybean, cotton, corn, peanut, sunflower, beat, wheat and the like, and moreover they are applied to vegetables such as lettuce, radish, tomato and the like without crop injury.

The m-phenoxybenzamide compounds (I) are useful as herbicides for, needless to say, paddy rice plants, and various cereals, beans, cotton, vegetables, orchards, turfs, pasture lands, tea gardens, mulberry farms, rubber plantations, woods and forests, non-crop lands and the like.

Further, they are low in toxicity to fishes and are high in safety to mammals.

In the above-mentioned description of the general formulae, the term "lower alkyl" means methyl, ethyl, n-propyl, isopropyl, n-butyl, isobutyl, sec-butyl, tert-butyl, n-amyl, isoamyl, 2-pentyl, 3-pentyl, neopentyl, 2-methylbutyl, n-hexyl, sec-hexyl, 1,3-dimethylbutyl, 3,3-dimethylbutyl, 2-methyl-1-pentyl, 3-methyl-2-pentyl, etc. The term "lower cycloalkyl" includes cyclopropyl, cyclopentyl, cyclohexyl, etc. The term "lower alkoxy" means methoxy, ethoxy, n-propoxy, isopropoxy, n-butoxy, etc. The term "lower alkenyl" means allyl, 1-methylallyl, 2-methylallyl, 2-butenyl and the like. The term "lower alkynyl" means propargyl, 3-butynyl, 1,1-dimethylpropynyl and the like. The term "lower alkoxy-substituted lower alkyl" means 2-methoxyethyl, 2-ethoxyethyl, 2-ethoxypropyl, 3-isopropoxypropyl and the like. The term "lower haloalkyl" includes 2-chloroethyl, 2-bromoethyl, 3-chloropropyl, 3-bromopropyl and the like. The term "lower cyanoalkyl" means cyanomethyl, 2-cyanoethyl, 3-cyanopropyl and the like. The term "lower alkylamino-substituted lower alkyl" means N,N-diethylaminoethyl, N,N-diethylaminopropyl, N,N-dibutylaminopropyl and the like. The term "halogen" is intended to mean fluorine, chlorine, bromine and iodide.

Among the m-phenoxybenzamide compounds (I), those having the formula (I'):

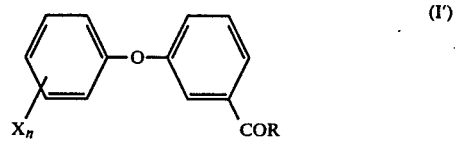

wherein X, which may be the same or different, is a fluorine, chlorine or bromine atom or a $C_1$–$C_4$ alkyl or $C_1$–$C_3$ alkoxy group, n is zero or an integer of 1 to 5 and R is a group of the formula:

(in which $R_1$ is a hydrogen atom, a $C_1$–$C_3$ alkyl or allyl group and $R_2$ is a $C_1$–$C_6$ alkyl, $C_3$–$C_4$ alkenyl, $C_3$–$C_5$ alkynyl, methoxy, $C_3$–$C_6$ cycloalkyl, bromoethyl, chloroethyl, $C_1$–$C_3$ alkoxy-substituted $C_2$–$C_3$ alkyl, cyano($C_1$–$C_2$)alkyl, di($C_1$–$C_4$)alkylamino-substituted $C_2$–$C_3$ alkyl or benzyl group) or an ethylenimino, pyrrolidino, dimethylpyrrolidino, piperidino, methylpiperidino, hexamethylenimino, morpholino or dimethylmorpholino group, are preferred as herbicides.

Particularly, the compounds of the formula (I"):

wherein X, which may be the same or different, is a fluorine, chlorine or bromine atom or a methyl, ethyl or methoxy group, n is an integer of 1 to 3 and R is a group of the formula:

(in which $R_1$ is a hydrogen atom or an ethyl group and $R_2$ is a $C_2$–$C_4$ alkyl, allyl, 1,1-dimethylpropynyl, cyclopropyl or methoxyethyl group) or a pyrrolidino group are most preferred because their herbicidal activity is the highest among the compounds of the present invention without phytotoxicity.

The m-phenoxybenzamide compounds (I) can be prepared by various processes, of which typical examples are as follows:

PROCESS I

The m-phenoxybenzamide compounds (I) are prepared by reacting a m-phenoxybenzoic acid of the formula (III'):

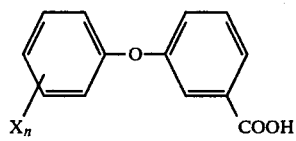
(III')

wherein X and n are each as defined above or its reactive derivative (e.g. acid halides, acid amides, acid anhydrides including mixed acid anhydrides, esters) with an amine of the formula (IV'):

(IV')

wherein $R_1$ and $R_2$ are each as defined above, or ethylenimine, pyrrolidine, dimethylpyrrolidine, piperidine, methylpiperidine, hexamethylenimine, morpholine or dimethylmorpholine.

This reaction may be carried out in the presence of a dehydrating agent or a condensing agent when the compound (III') is a free acid, or in the presence or absence of a dehydrohalogenating agent when the compound (III') is an acid halide. It is usually effected with cooling or heating or at room temperature with or without a solvent. Examples of the solvent include water, organic solvents (e.g. benzene, toluene, xylene, isopropanol, isobutanol, tert-butanol, diethyl ether, tetrahydrofuran, dioxane, dichloromethane, chloroform, carbon tetrachloride, ethyl acetate, pyridine, dimethylformamide, dimethylsulfoxide) and mixtures thereof.

As the dehydrating agent, for example, carbodiimides such as N,N'-dicyclohexylcarbodiimide may be used. As the condensing agent, for example, phosphorus oxychloride or thionyl chloride may be used. And, as the dehydrohalogenating agent, for example, alkali metal bicarbonates (e.g. sodium bicarbonate, potassium bicarbonate), alkali metal carbonates (e.g. sodium carbonate, potassium carbonate), trialkylamines (e.g. triethylamine, tributylamine) and bases (e.g. pyridine, pyrimidine) are preferably used.

The reaction time principally depends upon the reaction temperature and the kind of the reagent, but the reaction generally comes to an end within a moment to in 10 hours.

After the reaction is finished, the objective compound may be separated from the reaction mixture by conventional methods.

PROCESS II

The m-phenoxybenzamide compounds (I) are prepared by reacting a m-halobenzamide of the formula (V'):

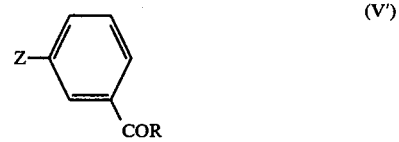
(V')

wherein R is as defined above and Z is a halogen atom with a phenol of the formula (VI'):

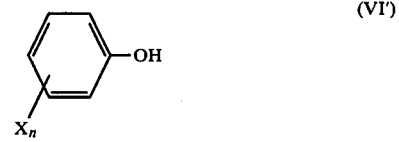
(VI')

wherein X and n are each as defined above.

This reaction may be carried out using a metallic compound as a catalyst in the presence of a dehydrohalogenating agent with or without an inert organic solvent. Examples of the inert organic solvent are benzene, toluene, xylene, dimethylformamide and dimethylsulfoxide, and mixtures thereof. The reaction is preferably carried out under reflux at the boiling point of the phenol (VI') when no solvent is used. When the solvent is used, the reaction is preferably carried out under reflux at the boiling point of the solvent.

The dehydrohalogenating agent includes, for example, alkali metal carbonates (e.g. sodium carbonate, potassium carbonate) and alkali metal hydroxides (e.g. sodium hydroxide, potassium hydroxide). As the metallic compound, for example, copper powder or cuprous chloride is preferably used.

The reaction time principally depends upon the reaction temperature and the kind of the reagent, but a time of 3 to 10 hours is generally preferred.

After the reaction is finished, the objective compound may be separated from the reaction mixture by conventional methods.

PROCESS III

The m-phenoxybenzamide compounds (I) are prepared by reacting a m-hydroxybenzamide of the formula (VII'):

(VII')

wherein R is as defined above with a halobenzene of the formula (VIII'):

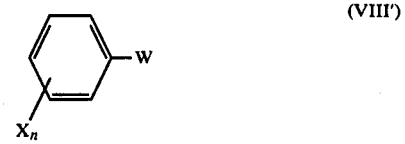
(VIII')

wherein X and n are each as defined above and W is a halogen atom.

This reaction may be carried out using a metallic compound as a catalyst in the presence of a dehydrohalogenating agent with or without an inert organic solvent. Examples of the inert organic solvent are benzene, toluene, xylene, dimethylformamide and dimethylsulfoxide, and mixtures thereof. The reaction is preferably carried out under reflux at the boiling point of the halobenzene when no solvent is used. When the solvent is used, the reaction is preferably carried out under reflux at the boiling point of the solvent.

The dehydrohalogenating agent includes, for example, alkali metal carbonates (e.g. sodium carbonate, potassium carbonate) and alkali metal hydroxides (e.g. sodium hydroxide, potassium hydroxide). As the metallic compound, for example, copper powder or cuprous chloride is preferably used.

The reaction time principally depends upon the reaction temperature and the kind of the reagent, but a time of 3 to 10 hours is generally preferred.

After the reaction is finished, the objective compound may be separated from the reaction mixture by conventional methods.

The compounds of the formulae (III'), (V') and (VII'), which are the starting materials in the above processes for production of the m-phenoxybenzamide compounds (I), can be easily produced by conventional methods, of which examples are as follows:

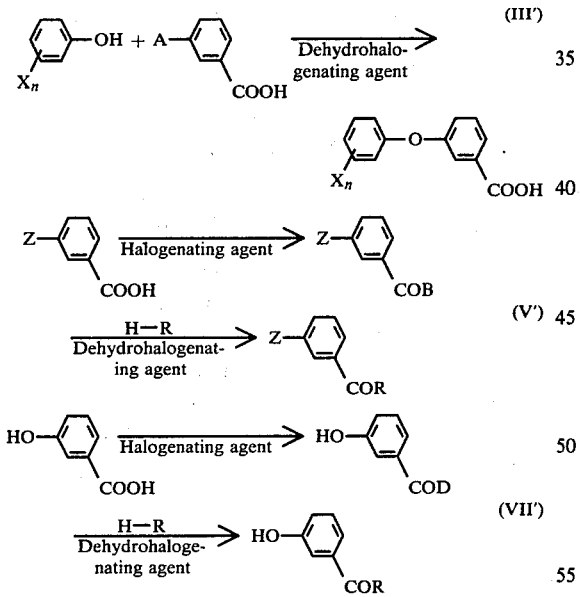

wherein R, X, Z and n are each as defined above and A, B and D are each a halogen atom.

The process for production of the m-phenoxybenzamide compounds (I) will be illustrated more in detail with reference to the following examples, which are however only given for the purpose of illustration and not to be interpreted as limiting the invention thereto.

EXAMPLE 1 (PROCESS I)

Ethyl acetate (50 ml) was added to 1.4 g of an aqueous ethylamine solution (70 %), and an ethyl acetate solution containing 3.0 g of 3-(2,5-dichlorophenoxy)-benzoic acid chloride was dropwise added thereto with stirring, during which the reaction mixture was cooled in an ice bath. After the addition was finished, the mixture was stirred for 1 hour at room temperature. The reaction mixture was washed with 1 N hydrochloric acid, water, 1% aqueous sodium hydroxide solution and water saturated with sodium chloride in this order and dried over anhydrous sodium sulfate. Thereafter, the solvent was removed by evaporation to obtain 3.1 g of crude crystals. On recrystallizing the crude crystals from a benzene-hexane mixed solvent, 2.8 g of N-ethyl-3-(2,5-dichlorophenoxy)benzamide were obtained. Melting point, 74.5°–75.5° C. Elementary analysis: Calcd. for $C_{15}H_{13}Cl_2NO_2$: C, 58.08%; H, 4.22%; N, 4.52%; Cl, 22.86%. Found: C, 58.16%; H, 4.25%; N, 4.49%; Cl, 22.97%. NMR: $\delta^{CCl_4}$: 1.15 (t 3H), 3.34 (quintet 2H), 6.65–7.61 (8H).

EXAMPLE 2 (PROCESS II)

N-Ethyl-3-bromobenzamide (11.4 g), 3-chloro-5-methoxyphenol (7.9 g) and potassium carbonate (3.8 g) were dissolved in 100 ml of dimethylformamide, and a catalytic amount of cuprous chloride was added thereto. The mixture was refluxed for 8 hours. After the reaction was finished, the reaction mixture was poured into 200 ml of water and extracted with ether. The ether extract was washed with 5% aqueous potassium hydroxide solution, water and an aqueous sodium chloride solution in this order and dried over anhydrous sodium sulfate. Thereafter, the solvent was removed by evaporation to obtain 11.6 g of an oily product. The oily product was passed through a column packed with silica gel and eluted with benzene to obtain 10.3 g of crude crystals. On recrystallizing the crude crystals from a benzene-hexane mixed solvent, 9.7 g of N-ethyl-3-(3-chloro-5-methoxyphenoxy)benzamide were obtained. Melting point, 80.5°–81.5° C. Elementary analysis: Calcd. for $C_{16}H_{16}ClNO_3$: C, 62.84%; H, 5.28%; N, 4.58%; Cl, 11.60%. Found: C, 62.81%; H, 5.28%; N, 4.59%; Cl, 11.66%. NMR: $\delta^{CCl_4}$: 1.16 (t 3H), 3.44 (quintet 2H), 3.69 ( s 3H), 6.20–7.52 (8H).

EXAMPLE 3 (PROCESS III)

N,N-Diethyl-m-oxybenzamide (19.3 g), m-bromotoluene (18.8 g), potassium carbonate (5.2 g) and sodium carbonate (4.0 g) were dissolved in 100 ml of dimethylformamide, and a catalytic amount of copper powder was added thereto. The mixture was refluxed for 5 hours. Thereafter, the reaction mixture was poured into 100 ml of water and extracted with ether. The ether extract was washed with 5% aqueous potassium hydroxide solution, water and an aqueous sodium chloride solution in this order and dried over anhydrous sodium sulfate. The solvent was then removed by evaporation to obtain 21.2 g of an oily product. The oily product was distilled to obtain 20.0 g of N,N-diethyl-3-(3-methylphenoxy)benzamide. Boiling point, 110°–114° C./0.1 mmHg. Elementary analysis: Calcd. for $C_{18}H_{21}NO_2$: C, 76.29%; H, 7.47%; N, 4.94%. Found: C, 75.97%; H, 7.50%; N, 4.93%. NMR: $\delta^{CCl_4}$: 1.13 (t 6H), 2.32 (s 3H), 3.30 (q 4H), 6.65–7.45 (8H).

Examples of the m-phenoxybenzamide compounds (I) produced in the same manner as in Examples 1, 2 and 3 (Processes I, II and III) are shown in Table 1.

TABLE 1

| Compound No. | Process | Compound | Physical property | Elementary analysis Calcd. (%) | Found (%) |
|---|---|---|---|---|---|
| 1 | I | Ph-O-C₆H₄-CON(CH₃)H | M.P. 95.5–96.5° C. | C 73.99<br>H 5.77<br>N 6.16 | C 74.08<br>H 5.79<br>N 6.20 |
| 2 | I | Ph-O-C₆H₄-CON(C₂H₅)H | M.P. 58–59° C. | C 74.66<br>H 6.27<br>N 5.81 | C 74.59<br>H 6.23<br>N 5.80 |
| 3 | II | Ph-O-C₆H₄-CON(C₃H₇(n))H | M.P. 62.5–64° C. | C 75.27<br>H 6.71<br>N 5.49 | C 75.50<br>H 6.68<br>N 5.50 |
| 4 | I | Ph-O-C₆H₄-CON(C₃H₇(iso))H | M.P. 100–101.5° C. | C 75.27<br>H 6.71<br>N 5.49 | C 75.12<br>H 6.70<br>N 5.52 |
| 5 | I | Ph-O-C₆H₄-CON(C₄H₉(n))H | M.P. 47–48° C. | C 75.81<br>H 7.11<br>N 5.20 | C 75.76<br>H 7.19<br>N 5.27 |
| 6 | I | Ph-O-C₆H₄-CON(C₄H₉(sec))H | M.P. 94.5–96° C. | C 75.81<br>H 7.11<br>N 5.20 | C 75.90<br>H 7.20<br>N 5.24 |
| 7 | I | Ph-O-C₆H₄-CON(C₄H₉(tert))H | M.P. 109–110° C. | C 75.81<br>H 7.11<br>N 5.20 | C 75.85<br>H 7.10<br>N 5.23 |
| 8 | III | Ph-O-C₆H₄-CON(C₆H₁₃(n))H | M.P. 56.5–57.5° C. | C 76.73<br>H 7.80<br>N 4.71 | C 76.91<br>H 7.80<br>N 4.75 |
| 9 | I | Ph-O-C₆H₄-CON(CH₃)(CH₃) | $[\eta]_D^{22.5}$ 1.5856 | C 74.66<br>H 6.27<br>N 5.81 | C 74.49<br>H 6.30<br>N 5.83 |
| 10 | I | Ph-O-C₆H₄-CON(C₂H₅)(C₂H₅) | B.P. 153–156° C./0.2 mmHg | C 75.81<br>H 7.11<br>N 5.20 | C 75.76<br>H 7.04<br>N 5.17 |
| 11 | III | Ph-O-C₆H₄-CON(C₃H₇(iso))(C₃H₇(iso)) | $[\eta]_D^{25}$ 1.5508 | C 76.73<br>H 7.80<br>N 4.71 | C 76.45<br>H 7.82<br>N 4.68 |
| 12 | I | Ph-O-C₆H₄-CON(OCH₃)(CH₃) | $[\eta]_D^{23.5}$ 1.5747 | C 70.02<br>H 5.88<br>N 5.44 | C 70.14<br>H 5.90<br>N 5.37 |

TABLE 1-continued

| Compound No. | Process | Compound | Physical property | Elementary analysis Calcd. (%) | | Found (%) | |
|---|---|---|---|---|---|---|---|
| 13 | II | 3-phenoxy-C(=O)NH-CH$_2$CH=CH$_2$ | M.P. 73.5–75° C. | C | 75.87 | C | 75.65 |
| | | | | H | 5.97 | H | 5.95 |
| | | | | N | 5.53 | N | 5.50 |
| 14 | II | 3-phenoxy-C(=O)N(CH$_2$CH=CH$_2$)$_2$ | M.P. 37–38.5° C. | C | 77.79 | C | 77.90 |
| | | | | H | 6.53 | H | 6.47 |
| | | | | N | 4.77 | N | 4.81 |
| 15 | I | 3-phenoxy-C(=O)NH-CH$_2$C(CH$_3$)=CH$_2$ | M.P. 74–75° C. | C | 76.38 | C | 76.40 |
| | | | | H | 6.41 | H | 6.37 |
| | | | | N | 5.24 | N | 5.22 |
| 16 | I | 3-phenoxy-C(=O)N(CH$_3$)-CH$_2$C≡CH | B.P. 143–148° C./0.1 mmHg | C | 76.96 | C | 77.03 |
| | | | | H | 5.70 | H | 5.65 |
| | | | | N | 5.28 | N | 5.26 |
| 17 | I | 3-phenoxy-C(=O)NH-CH$_2$CH$_2$OCH$_3$ | M.P. 69–70° C. | C | 70.83 | C | 70.70 |
| | | | | H | 6.32 | H | 6.30 |
| | | | | N | 5.16 | N | 5.18 |
| 18 | I | 3-phenoxy-C(=O)NH-(CH$_2$)$_3$OC$_2$H$_5$ | B.P. 184–186° C./0.3 mmHg | C | 72.21 | C | 72.16 |
| | | | | H | 7.07 | H | 7.03 |
| | | | | N | 4.68 | N | 4.56 |
| 19 | I | 3-phenoxy-C(=O)NH-(CH$_2$)$_3$OC$_3$H$_7$(iso) | B.P. 176–180° C./0.1 mmHg | C | 72.82 | C | 72.90 |
| | | | | H | 7.40 | H | 7.42 |
| | | | | N | 4.47 | N | 4.50 |
| 20 | I | 3-phenoxy-C(=O)NH-(CH$_2$)$_2$N(C$_2$H$_5$)$_2$ | B.P. 157–162° C./0.1 mmHg | C | 73.04 | C | 72.89 |
| | | | | H | 7.74 | H | 7.72 |
| | | | | N | 8.97 | N | 8.99 |
| 21 | II | 3-phenoxy-C(=O)NH-(CH$_2$)$_3$N(CH$_3$)$_2$ | B.P. 173–177° C./0.2 mmHg | C | 72.45 | C | 72.29 |
| | | | | H | 7.43 | H | 7.38 |
| | | | | N | 9.39 | N | 9.32 |
| 22 | I | 3-phenoxy-C(=O)NH-(CH$_2$)$_3$N(C$_4$H$_9$(n))$_2$ | B.P. 200–205° C./0.2 mmHg | C | 75.35 | C | 75.51 |
| | | | | H | 8.96 | H | 8.92 |
| | | | | N | 7.32 | N | 7.13 |
| 23 | I | 3-phenoxy-C(=O)NH-CH$_2$CH$_2$Cl | M.P. 85–86° C. | C | 65.34 | C | 65.20 |
| | | | | H | 5.12 | H | 5.09 |
| | | | | N | 5.08 | N | 5.10 |
| | | | | Cl | 12.86 | Cl | 12.91 |
| 24 | I | 3-phenoxy-C(=O)NH-CH$_2$CH$_2$Br | M.P. 76–77.5° C. | C | 56.27 | C | 56.17 |
| | | | | H | 4.41 | H | 4.39 |
| | | | | N | 4.39 | N | 4.44 |
| | | | | Br | 24.96 | Br | 25.05 |

TABLE 1-continued

| Compound No. | Process | Compound | Physical property | Elementary analysis Calcd. (%) | Found (%) |
|---|---|---|---|---|---|
| 25 | I | (phenoxyphenyl)-CON(aziridine) | B.P. 147-148° C./ 0.5 mmHg | C 75.30<br>H 5.40<br>N 5.85 | C 75.53<br>H 5.51<br>N 5.82 |
| 26 | III | (phenoxyphenyl)-CON(piperidine) | M.P. 59.5-60.5° C. | C 76.38<br>H 6.41<br>N 5.24 | C 76.43<br>H 6.43<br>N 5.22 |
| 27 | II | (phenoxyphenyl)-CON(2,5-dimethylpiperidine) | $[\eta]_D^{22}$ 1.5678 | C 77.26<br>H 7.17<br>N 4.74 | C 77.20<br>H 7.23<br>N 4.76 |
| 28 | III | (phenoxyphenyl)-CON(hexamethyleneimine) | M.P. 80-81° C. | C 76.84<br>H 6.81<br>N 4.98 | C 76.57<br>H 6.78<br>N 4.98 |
| 29 | I | (phenoxyphenyl)-CON(azepane) | B.P. 155-156° C./ 0.1 mmHg | C 77.26<br>H 7.17<br>N 4.74 | C 77.19<br>H 7.19<br>N 4.70 |
| 30 | I | (phenoxyphenyl)-CON(morpholine) | M.P. 53.5-54.5° C. | C 72.06<br>H 6.05<br>N 4.94 | C 72.21<br>H 6.04<br>N 4.92 |
| 31 | III | (phenoxyphenyl)-CONH-CH₂-phenyl | M.P. 94-95.5° C. | C 79.18<br>H 5.65<br>N 4.62 | C 79.10<br>H 5.62<br>N 4.59 |
| 32 | I | (phenoxyphenyl)-CONH-CH₂CN | M.P. 92-93° C. | C 71.41<br>H 4.80<br>N 11.11 | C 71.36<br>H 4.75<br>N 11.09 |
| 33 | I | (2-methylphenoxy-phenyl)-CONH-C₃H₇(iso) | M.P. 136-137° C. | C 75.81<br>H 7.11<br>N 5.20 | C 75.69<br>H 7.03<br>N 5.25 |
| 34 | I | (2-methylphenoxy-phenyl)-CON(piperidine) | B.P. 152-160° C./ 0.15 mmHg | C 76.84<br>H 6.81<br>N 4.98 | C 76.69<br>H 6.79<br>N 4.99 |
| 35 | I | (2-methylphenoxy-phenyl)-CONH-CH₂CH₂CN | M.P. 94-95° C. | C 72.84<br>H 5.75<br>N 9.99 | C 72.80<br>H 5.70<br>N 9.96 |
| 36 | II | (3-methylphenoxy-phenyl)-CONH-C₂H₅ | M.P. 58.5-59° C. | C 75.27<br>H 6.71<br>N 5.49 | C 75.38<br>H 6.75<br>N 5.51 |

TABLE 1-continued

| Compound No. | Process | Compound | Physical property | Elementary analysis Calcd. (%) | Found (%) |
|---|---|---|---|---|---|
| 37 | I | 3-CH₃-C₆H₄-O-C₆H₄-CONH-C₃H₇(iso) | M.P. 111–112° C. | C 75.81 H 7.11 N 5.20 | C 75.69 H 7.07 N 5.18 |
| 38 | I | 3-CH₃-C₆H₄-O-C₆H₄-CONH-C₄H₉(tert) | M.P. 66–67.5° C. | C 76.29 H 7.47 N 4.94 | C 76.24 H 7.38 N 4.99 |
| 39 | III | 3-CH₃-C₆H₄-O-C₆H₄-CO-N(piperidine) | B.P. 169–173° C./0.1 mmHg | C 76.84 H 6.81 N 4.98 | C 76.79 H 6.75 N 4.95 |
| 40 | III | 3-CH₃-C₆H₄-O-C₆H₄-CON(C₂H₅)₂ | B.P. 110–114° C./0.1 mmHg | C 76.29 H 7.47 N 4.94 | C 75.97 H 7.50 N 4.93 |
| 41 | I | 4-CH₃-C₆H₄-O-C₆H₄-CONH-C₂H₅ | M.P. 69.5–70° C. | C 75.27 H 6.71 N 5.49 | C 75.22 H 6.69 N 5.53 |
| 42 | I | 4-CH₃-C₆H₄-O-C₆H₄-CONH-C₃H₇(iso) | M.P. 88.5–90° C. | C 75.81 H 7.11 N 5.20 | C 75.90 H 7.16 N 5.15 |
| 43 | I | 4-CH₃-C₆H₄-O-C₆H₄-CONH-C₄H₉(tert) | M.P. 62.5–64° C. | C 76.29 H 7.47 N 4.94 | C 76.36 H 7.49 N 4.92 |
| 44 | II | 4-CH₃-C₆H₄-O-C₆H₄-CO-N(piperidine) | B.P. 175–177° C./0.1 mmHg | C 76.84 H 6.81 N 4.98 | C 76.80 H 6.89 N 4.97 |
| 45 | I | 4-CH₃-C₆H₄-O-C₆H₄-CONH-CH₂CH₂Cl | B.P. 150–155° C./0.08 mmHg | C 66.32 H 5.57 N 4.84 Cl 12.24 | C 66.35 H 5.61 N 4.83 Cl 12.20 |
| 46 | I | 4-CH₃-C₆H₄-O-C₆H₄-CO-N(2,6-dimethylmorpholine) | B.P. 131–140° C./0.1 mmHg | C 73.82 H 7.12 N 4.30 | C 73.73 H 7.19 N 4.27 |
| 47 | II | 2,3-(CH₃)₂-C₆H₃-O-C₆H₄-CONH-C₃H₇(iso) | M.P. 154–155.5° C. | C 76.29 H 7.47 N 4.94 | C 76.43 H 7.50 N 4.89 |
| 48 | I | 2,4-(CH₃)₂-C₆H₃-O-C₆H₄-CONH-C₃H₇(iso) | M.P. 122–124° C. | C 76.29 H 7.47 N 4.94 | C 76.19 H 7.43 N 4.96 |

TABLE 1-continued

| Compound No. | Process | Compound | Physical property | Calcd. (%) | Found (%) |
|---|---|---|---|---|---|
| 49 | I | 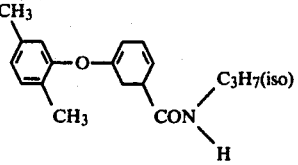 | M.P. 106–107° C. | C 76.29<br>H 7.47<br>N 4.94 | C 76.34<br>H 7.50<br>N 4.95 |
| 50 | II | 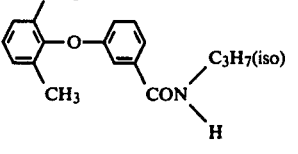 | M.P. 127–128.5° C. | C 76.29<br>H 7.47<br>N 4.94 | C 76.22<br>H 7.50<br>N 4.99 |
| 51 | I | 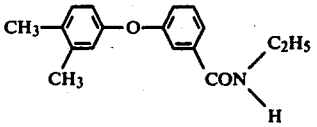 | B.P 160–162° C./ 0.08 mmHg | C 75.81<br>H 7.11<br>N 5.20 | C 75.71<br>H 7.13<br>N 5.18 |
| 52 | I | 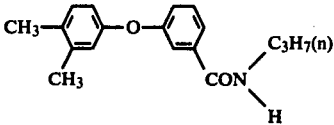 | B.P. 180–185° C./ 0.2 mmHg | C 76.29<br>H 7.47<br>N 4.94 | C 76.20<br>H 7.51<br>N 5.01 |
| 53 | I | 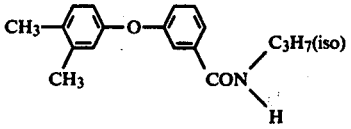 | M.P. 94.5–96° C. | C 76.29<br>H 7.47<br>N 4.94 | C 76.32<br>H 7.49<br>N 4.85 |
| 54 | II | 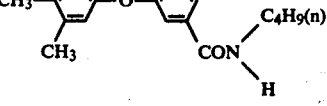 | B.P. 190–195° C./ 0.15 mmHg | C 76.73<br>H 7.80<br>N 4.71 | C 76.64<br>H 7.84<br>N 4.68 |
| 55 | II |  | B.P. 184–186° C./ 0.2 mmHg | C 77.26<br>H 7.17<br>N 4.74 | C 77.51<br>H 7.30<br>N 4.71 |
| 56 | I | 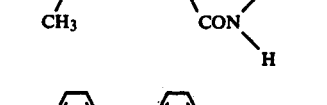 | B.P. 174–185° C./ 0.2 mmHg | C 76.84<br>H 6.81<br>N 4.98 | C 76.69<br>H 6.78<br>N 5.01 |
| 57 | I | 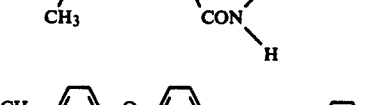 | B.P. 165–175° C./ 0.2 mmHg | C 72.70<br>H 6.44<br>N 4.71 | C 72.66<br>H 6.39<br>N 4.65 |
| 58 | III |  | M.P. 79–80° C. | C 79.73<br>H 6.39<br>N 4.23 | C 79.87<br>H 6.42<br>N 4.27 |
| 59 | I | 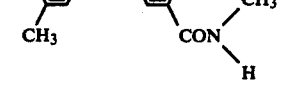 | M.P. 87–88° C. | C 75.27<br>H 6.71<br>N 5.49 | C 75.37<br>H 6.67<br>N 5.50 |

TABLE 1-continued

| Compound No. | Process | Compound | Physical property | Elementary analysis Calcd. (%) | | Found (%) | |
|---|---|---|---|---|---|---|---|
| 60 | I | 3,5-dimethylphenyl-O-phenyl-CONH-C$_2$H$_5$ | M.P. 104.5–105.5° C. | C H N | 75.81 7.11 5.20 | C H N | 75.80 7.10 5.23 |
| 61 | I | 3,5-dimethylphenyl-O-phenyl-CONH-C$_3$H$_7$(n) | M.P. 94–95° C. | C H N | 76.29 7.47 4.94 | C H N | 76.33 7.48 4.98 |
| 62 | I | 3,5-dimethylphenyl-O-phenyl-CONH-C$_3$H$_7$(iso) | M.P. 126.5–128° C. | C H N | 76.29 7.47 4.94 | C H N | 76.37 7.52 4.92 |
| 63 | I | 3,5-dimethylphenyl-O-phenyl-CONH-C$_5$H$_{11}$(neo) | M.P. 94–95° C. | C H N | 77.13 8.09 4.50 | C H N | 77.09 8.10 4.46 |
| 64 | II | 3,5-dimethylphenyl-O-phenyl-CON(C$_2$H$_5$)$_2$ | B.P. 145–147° C./ 0.2 mmHg | C H N | 76.73 7.80 4.71 | C H N | 76.78 7.78 4.68 |
| 65 | II | 3,5-dimethylphenyl-O-phenyl-CON(piperidine) | B.P. 140–142° C./ 0.1 mmHg | C H N | 77.26 7.17 4.74 | C H N | 77.20 7.15 4.61 |
| 66 | I | 2,3-dimethylphenyl-O-phenyl-CONH-C$_3$H$_7$(iso) | M.P. 143–144.5° C. | C H N | 76.73 7.80 4.71 | C H N | 76.68 7.84 4.67 |
| 67 | I | 2,4,5-trimethylphenyl-O-phenyl-CONH-C$_2$H$_5$ | M.P. 99.5–100° C. | C H N | 76.29 7.47 4.94 | C H N | 76.33 7.51 4.89 |
| 68 | I | 2,4,5-trimethylphenyl-O-phenyl-CONH-C$_3$H$_7$(iso) | B.P. 153–156° C./ 0.08 mmHg | C H N | 76.73 7.80 4.71 | C H N | 76.77 7.82 4.68 |
| 69 | I | (iso)C$_3$H$_7$-phenyl-O-phenyl-CON(CH$_3$)H | B.P. 173–175° C./ 0.3 mmHg | C H N | 75.81 7.11 5.20 | C H N | 75.69 7.08 5.25 |

TABLE 1-continued

| Compound No. | Process | Compound | Physical property | Elementary analysis Calcd. (%) | | Found (%) | |
|---|---|---|---|---|---|---|---|
| 70 | I | (iso)C₃H₇-C₆H₃-O-C₆H₄-CON(H)C₂H₅ | B.P. 165–175° C./ 0.3 mmHg | C | 76.29 | C | 76.33 |
|  |  |  |  | H | 7.47 | H | 7.50 |
|  |  |  |  | N | 4.94 | N | 4.90 |
| 71 | I | (iso)C₃H₇-C₆H₃-O-C₆H₄-CON(H)C₃H₇(iso) | B.P 149–151° C./ 0.3 mmHg | C | 76.73 | C | 76.64 |
|  |  |  |  | H | 7.80 | H | 7.78 |
|  |  |  |  | N | 4.71 | N | 4.72 |
| 72 | II | (sec)C₄H₉-C₆H₄-O-C₆H₄-CON(H)C₃H₇(iso) | B.P. 130–136° C./ 0.1 mmHg | C | 77.13 | C | 77.08 |
|  |  |  |  | H | 8.09 | H | 8.07 |
|  |  |  |  | N | 4.50 | N | 4.55 |
| 73 | I | (tert)C₄H₉-C₆H₃-O-C₆H₄-CON(H)C₃H₇(iso) | M.P. 82–83° C. | C | 77.13 | C | 77.12 |
|  |  |  |  | H | 8.09 | H | 8.11 |
|  |  |  |  | N | 4.50 | N | 4.48 |
| 74 | I | OCH₃-C₆H₄-O-C₆H₄-CON(H)CH₃ | M.P. 91–92° C. | C | 70.02 | C | 70.08 |
|  |  |  |  | H | 5.88 | H | 5.90 |
|  |  |  |  | N | 5.44 | N | 5.39 |
| 75 | I | OCH₃-C₆H₄-O-C₆H₄-CON(H)C₂H₅ | M.P. 99–102° C. | C | 70.83 | C | 70.76 |
|  |  |  |  | H | 6.32 | H | 6.32 |
|  |  |  |  | N | 5.16 | N | 5.18 |
| 76 | I | OCH₃-C₆H₄-O-C₆H₄-CON(H)C₃H₇(iso) | M.P. 126–127° C. | C | 71.56 | C | 71.60 |
|  |  |  |  | H | 6.71 | H | 6.72 |
|  |  |  |  | N | 4.91 | N | 4.90 |
| 77 | I | OCH₃-C₆H₄-O-C₆H₄-CON(H)CH₂C≡CH | M.P. 93.5–94° C. | C | 72.58 | C | 72.59 |
|  |  |  |  | H | 5.37 | H | 5.40 |
|  |  |  |  | N | 4.98 | N | 5.00 |
| 78 | I | OCH₃-C₆H₄-O-C₆H₄-CON(H)CH₂CH₂OCH₃ | M.P. 62–63° C. | C | 67.76 | C | 67.71 |
|  |  |  |  | H | 6.36 | H | 6.41 |
|  |  |  |  | N | 4.65 | N | 4.60 |
| 79 | I | CH₃O-C₆H₄-O-C₆H₄-CON(H)C₂H₅ | $[\eta]_D^{24.5}$ 1.5822 | C | 70.83 | C | 70.77 |
|  |  |  |  | H | 6.32 | H | 6.31 |
|  |  |  |  | N | 5.16 | N | 5.18 |
| 80 | I | CH₃O-C₆H₄-O-C₆H₄-CON(H)C₃H₇(iso) | M.P. 83–85° C. | C | 71.56 | C | 71.59 |
|  |  |  |  | H | 6.71 | H | 6.67 |
|  |  |  |  | N | 4.91 | N | 4.91 |
| 81 | I | CH₃O-C₆H₄-O-C₆H₄-CON(H)CH₂CH=CH₂ | B.P. 170–173° C./ 0.07 mmHg | C | 72.06 | C | 72.18 |
|  |  |  |  | H | 6.05 | H | 6.04 |
|  |  |  |  | N | 4.94 | N | 4.97 |

TABLE 1-continued

| Compound No. | Process | Compound | Physical property | Elementary analysis Calcd. (%) | Found (%) |
|---|---|---|---|---|---|
| 82 | I | 3-CH₃O-phenyl-O-phenyl-CON(2-methylpiperidine) | B.P. 142–152° C./ 0.1 mmHg | C 73.82 H 7.12 N 4.30 | C 73.98 H 7.10 N 4.33 |
| 83 | I | 4-CH₃O-phenyl-O-phenyl-CONH-C₂H₅ | M.P. 62–63.5° C. | C 70.83 H 6.32 N 5.16 | C 70.77 H 6.34 N 5.15 |
| 84 | I | 4-CH₃O-phenyl-O-phenyl-CONH-C₃H₇(iso) | M.P. 84–86° C. | C 71.56 H 6.71 N 4.91 | C 71.49 H 6.75 N 4.94 |
| 85 | I | 4-CH₃O-phenyl-O-phenyl-CONH-C₄H₉(tert) | M.P. 97–99° C. | C 72.21 H 7.07 N 4.68 | C 72.28 H 7.05 N 4.63 |
| 86 | I | 3,4-(CH₃)₂-phenyl-O-phenyl-CONH-C₄H₉(tert) | M.P. 100–101° C. | C 76.73 H 7.80 N 4.71 | C 76.75 H 7.86 N 4.79 |
| 87 | II | 3,5-(CH₃O)₂-phenyl-O-phenyl-CONH-C₃H₇(iso) | M.P. 111–114° C. | C 68.55 H 6.71 N 4.44 | C 68.49 H 6.68 N 4.41 |
| 88 | II | 3-C₂H₅O-phenyl-O-phenyl-CONH-C₂H₅ | B.P. 183–185° C./ 0.15 mmHg | C 71.56 H 6.71 N 4.91 | C 71.55 H 6.71 N 4.89 |
| 89 | II | 3-C₂H₅O-phenyl-O-phenyl-CONH-C₃H₇(iso) | M.P. 81–82° C. | C 72.21 H 7.07 N 4.68 | C 72.12 H 7.10 N 4.69 |
| 90 | II | 3-(iso)C₃H₇O-phenyl-O-phenyl-CONH-C₃H₇(iso) | B.P. 164–168° C./ 0.1 mmHg | C 72.82 H 7.40 N 4.47 | C 72.79 H 7.42 N 4.35 |
| 91 | I | 4-CH₃-2-OCH₃-phenyl-O-phenyl-CONH-C₂H₅ | B.P. 160–168° C./ 0.1 mmHg | C 71.56 H 6.71 N 4.91 | C 71.44 H 6.79 N 4.86 |
| 92 | I | 4-CH₃-2-OCH₃-phenyl-O-phenyl-CONH-C₃H₇(iso) | M.P. 67–68° C. | C 72.21 H 7.07 N 4.68 | C 72.18 H 7.06 N 4.68 |

TABLE 1-continued

| Compound No. | Process | Compound | Physical property | Elementary analysis Calcd. (%) | Found (%) |
|---|---|---|---|---|---|
| 93 | I | (iso)C₃H₇O—⟨⟩—O—⟨⟩—CON(H)C₄H₉(tert) | M.P. 107–109° C. | C 73.36 H 7.07 N 4.28 | C 73.42 H 7.09 N 4.31 |
| 94 | I | CH₃—⟨⟩(CH₃)—O—⟨⟩—CON(H)C₂H₅ | M.P. 61–63° C. | C 75.81 H 7.11 N 5.20 | C 75.79 H 7.10 N 5.27 |
| 95 | I | CH₃—⟨⟩(CH₃)—O—⟨⟩—CON(H)C₄H₉(tert) | M.P. 97–98.5° C. | C 76.73 H 7.80 N 4.71 | C 76.68 H 7.84 N 4.69 |
| 96 | I | CH₃/CH₃—⟨⟩—O—⟨⟩—CON(H)C₂H₅ | M.P. 60–61° C. | C 75.81 H 7.11 N 5.20 | C 75.80 H 7.12 N 5.18 |
| 97 | I | CH₃/CH₃—⟨⟩—O—⟨⟩—CON(H)C₄H₉(tert) | M.P. 104–105.5° C. | C 76.73 H 7.80 N 4.71 | C 76.64 H 7.76 N 4.70 |
| 98 | I | CH₃/CH₃—⟨⟩—O—⟨⟩—CON(H)C₄H₉(tert) | M.P. 101–102° C. | C 76.73 H 7.80 N 4.71 | C 76.65 H 7.83 N 4.68 |
| 99 | I | CH₃/CH₃/CH₃—⟨⟩—O—⟨⟩—CON(H)C₂H₅ | M.P. 100.5–101° C. | C 76.29 H 7.47 N 4.94 | C 76.27 H 7.44 N 4.85 |
| 100 | I | CH₃/CH₃/CH₃—⟨⟩—O—⟨⟩—CON(H)C₄H₉(tert) | M.P. 117.5–118° C. | C 77.13 H 8.09 N 4.50 | C 77.08 H 8.13 N 4.48 |
| 101 | II | CH₃O/CH₃O—⟨⟩—O—⟨⟩—CON(H)C₂H₅ | B.P. 190–195° C./0.2 mmHg | C 67.76 H 6.36 N 4.65 | C 67.77 H 6.39 N 4.78 |
| 102 | I | ⟨⟩(C₂H₅)—O—⟨⟩—CON(H)C₂H₅ | B.P. 166–170° C./0.15 mmHg | C 75.81 H 7.11 N 5.20 | C 75.82 H 7.10 N 5.24 |
| 103 | I | ⟨⟩(C₂H₅)—O—⟨⟩—CON(H)C₃H₇(iso) | M.P. 102.5–104° C. | C 76.29 H 7.47 N 4.94 | C 76.31 H 7.43 N 4.96 |

TABLE 1-continued

| Compound No. | Process | Compound | Physical property | Elementary analysis Calcd. (%) | Found (%) |
|---|---|---|---|---|---|
| 104 | I | 2-ethylphenyl-O-phenyl, CON(H)C₄H₉(tert) | M.P. 82–83° C. | C 76.73<br>H 7.80<br>N 4.71 | C 76.67<br>H 7.82<br>N 4.72 |
| 105 | I | 2-OC₂H₅-phenyl-O-phenyl, CON(H)C₂H₅ | M.P. 88–89° C. | C 71.56<br>H 6.71<br>N 4.91 | C 71.59<br>H 6.79<br>N 4.90 |
| 106 | I | 2-OC₂H₅-phenyl-O-phenyl, CON(H)C₃H₇(iso) | M.P. 85–86° C. | C 72.21<br>H 7.07<br>N 4.68 | C 72.29<br>H 7.06<br>N 4.63 |
| 107 | I | 2-OC₂H₅-phenyl-O-phenyl, CON(H)C₄H₉(tert) | M.P. 103–104° C. | C 72.82<br>H 7.40<br>N 4.47 | C 72.80<br>H 7.36<br>N 4.59 |
| 108 | II | 2-OC₃H₇(iso)-phenyl-O-phenyl, CON(H)C₂H₅ | M.P. 83.5–84° C. | C 72.21<br>H 7.07<br>N 4.68 | C 72.32<br>H 7.03<br>N 4.70 |
| 109 | II | 2-OC₃H₇(iso)-phenyl-O-phenyl, CON(H)C₃H₇(iso) | M.P. 109.5–110° C. | C 72.82<br>H 7.40<br>N 4.47 | C 72.83<br>H 7.39<br>N 4.49 |
| 110 | II | 2-OC₃H₇(iso)-phenyl-O-phenyl, CON(H)C₄H₉(tert) | M.P. 62–63° C. | C 73.36<br>H 7.70<br>N 4.28 | C 73.40<br>H 7.72<br>N 4.30 |
| 111 | I | 4-CH₃-2-OCH₃-phenyl-O-phenyl, CON(H)C₂H₅ | M.P. 102.5–104° C. | C 71.56<br>H 6.71<br>N 4.91 | C 71.61<br>H 6.71<br>N 4.95 |
| 112 | I | 4-CH₃-2-OCH₃-phenyl-O-phenyl, CON(H)C₃H₇(iso) | M.P. 128–130° C. | C 72.21<br>H 7.07<br>N 4.68 | C 72.18<br>H 7.15<br>N 4.73 |
| 113 | I | 4-CH₃-2-OCH₃-phenyl-O-phenyl, CON(H)C₄H₉(tert) | M.P. 141–142° C. | C 72.82<br>H 7.40<br>N 4.47 | C 72.27<br>H 7.51<br>N 4.46 |
| 114 | I | 3,5-(CH₃)₂-2-OCH₃-phenyl-O-phenyl (likely 4-CH₃-3-CH₃-2-OCH₃), CON(H)C₂H₅ | B.P. 180–183° C./ 0.2 mmHg | C 72.21<br>H 7.07<br>N 4.68 | C 72.15<br>H 7.10<br>N 4.78 |

TABLE 1-continued

| Compound No. | Process | Compound | Physical property | Elementary analysis Calcd. (%) | Found (%) |
|---|---|---|---|---|---|
| 115 | I | 2,4-dimethyl-6-methoxy-phenoxy-phenyl-CON(H)-C3H7(iso) | M.P. 76–77° C. | C 72.82 H 7.40 N 4.28 | C 72.89 H 7.45 N 4.24 |
| 116 | I | 2,4-dimethyl-6-methoxy-phenoxy-phenyl-CON(H)-C4H9(tert) | M.P. 108–109° C. | C 73.36 H 7.70 N 4.28 | C 73.30 H 7.65 N 4.31 |
| 117 | I | 2,4-dimethyl-phenoxy-phenyl-CON(H)-cyclopropyl | M.P. 128.5–129.5° C. | C 76.84 H 6.81 N 4.98 | C 76.78 H 6.79 N 5.03 |
| 118 | I | 3-ethoxy-phenoxy-phenyl-CON(H)-cyclohexyl | B.P. 188–192° C./ 0.1 mmHg | C 74.31 H 7.42 N 4.13 | C 74.27 H 7.44 N 4.16 |
| 119 | I | 2,4-dimethyl-phenoxy-phenyl-CON(H)-CH3 | M.P. 89–91° C. | C 75.27 H 6.71 N 5.49 | C 75.23 H 6.68 N 5.52 |
| 120 | I | 2,4,6-trimethyl-phenoxy-phenyl-CON(H)-CH3 | M.P. 127–129° C. | C 75.81 H 7.11 N 5.20 | C 75.80 H 7.10 N 5.23 |
| 121 | II | 2-chloro-phenoxy-phenyl-CON(H)-C2H5 | B.P. 140–146° C./ 0.1 mmHg | C 65.34 H 5.12 N 5.08 Cl 12.86 | C 65.30 H 5.11 N 5.04 Cl 12.82 |
| 122 | II | 2-chloro-phenoxy-phenyl-CON(H)-C3H7(iso) | M.P. 130–131° C. | C 66.32 H 5.57 N 4.84 Cl 12.24 | C 66.20 H 5.62 N 4.81 Cl 12.19 |
| 123 | I | 3-chloro-phenoxy-phenyl-CON(H)-C2H5 | B.P. 162–165° C./ 0.2 mmHg | C 65.34 H 5.12 N 5.08 Cl 12.86 | C 65.43 H 5.15 N 5.08 Cl 12.88 |
| 124 | I | 3-chloro-phenoxy-phenyl-CON(H)-C3H7(iso) | M.P. 127–129° C. | C 66.32 H 5.57 N 4.84 Cl 12.24 | C 66.27 H 5.60 N 4.82 Cl 12.29 |
| 125 | I | 3-chloro-phenoxy-phenyl-CON(H)-C4H9(tert) | M.P. 81.5–82° C. | C 67.21 H 5.97 N 4.61 Cl 11.67 | C 67.20 H 6.00 N 4.64 Cl 11.67 |

TABLE 1-continued

| Compound No. | Process | Compound | Physical property | Elementary analysis Calcd. (%) | Found (%) |
|---|---|---|---|---|---|
| 126 | I | Cl—⟨⟩—O—⟨⟩—CONH—C₂H₅ | M.P. 69–73° C. | C 65.34 H 5.12 N 5.08 Cl 12.86 | C 65.45 H 5.10 N 5.11 Cl 12.92 |
| 127 | I | Cl—⟨⟩—O—⟨⟩—CONH—C₃H₇(iso) | M.P. 105.5–107° C. | C 66.32 H 5.57 N 4.84 Cl 12.24 | C 66.22 H 5.52 N 4.86 Cl 12.29 |
| 128 | I | Cl—⟨⟩—O—⟨⟩—CONH—C₄H₉(tert) | M.P. 94.5–97.5° C. | C 67.21 H 5.97 N 4.61 Cl 11.67 | C 67.18 H 5.94 N 4.58 Cl 11.63 |
| 129 | I | Cl—⟨⟩—O—⟨⟩—CON(piperidine) | B.P. 170–180° C./0.1 mmHg | C 67.66 H 5.34 N 4.64 Cl 11.75 | C 67.83 H 5.37 N 4.61 Cl 11.70 |
| 130 | I | 2-F-⟨⟩—O—⟨⟩—CONH—C₂H₅ | M.P. 104.5–106° C. | C 69.48 H 5.44 N 5.40 | C 69.55 H 5.41 N 5.52 |
| 131 | I | 2-F-⟨⟩—O—⟨⟩—CONH—C₃H₇(iso) | M.P. 107.5–109° C. | C 70.31 H 5.90 N 5.13 | C 70.39 H 5.88 N 5.09 |
| 132 | I | 2-F-⟨⟩—O—⟨⟩—CONH—C₄H₉(tert) | M.P. 118–118.5° C. | C 71.06 H 6.31 N 4.88 | C 71.15 H 6.23 N 4.90 |
| 133 | I | 2-F-⟨⟩—O—⟨⟩—CONH—C(CH₃)₂—C≡CH | M.P. 112–113° C. | C 72.71 H 5.43 N 4.71 | C 72.70 H 5.46 N 4.83 |
| 134 | I | 3-F-⟨⟩—O—⟨⟩—CONH—C₂H₅ | M.P. 77–78° C. | C 69.48 H 5.44 N 5.40 | C 69.57 H 5.42 N 5.37 |
| 135 | I | 3-F-⟨⟩—O—⟨⟩—CONH—C₃H₇(iso) | M.P. 127–128.5° C. | C 70.31 H 5.90 N 5.13 | C 70.28 H 5.93 N 5.09 |
| 136 | I | 3-F-⟨⟩—O—⟨⟩—CONH—C₄H₉(tert) | M.P. 111–112° C. | C 71.06 H 6.31 N 4.88 | C 71.12 H 6.28 N 4.92 |
| 137 | III | F—⟨⟩—O—⟨⟩—CONH—C₃H₇(iso) | M.P. 103–104° C. | C 70.31 H 5.90 N 5.13 | C 70.22 H 5.96 N 5.15 |

TABLE 1-continued

| Compound No. | Process | Compound | Physical property | Elementary analysis Calcd. (%) | Found (%) |
|---|---|---|---|---|---|
| 138 | III | Br—⟨⟩—O—⟨⟩—CON(C₂H₅)H | M.P. 91.5–93° C. | C 56.27<br>H 4.41<br>N 4.39<br>Br 24.96 | C 56.42<br>H 4.36<br>N 4.42<br>Br 25.05 |
| 139 | III | Br—⟨⟩—O—⟨⟩—CON(C₃H₇(iso))H | M.P. 120–121° C. | C 57.50<br>H 4.83<br>N 4.19<br>Br 23.91 | C 57.43<br>H 4.87<br>N 4.22<br>Br 23.89 |
| 140 | I | Br—⟨⟩—O—⟨⟩—CON(C₄H₉(tert))H | M.P. 98–99° C. | C 58.63<br>H 5.22<br>N 4.02<br>Br 22.94 | C 58.55<br>H 5.26<br>N 4.00<br>Br 22.85 |
| 141 | I | (2,3-Cl₂)⟨⟩—O—⟨⟩—CON(C₂H₅)H | $[\eta]_D^{23}$ 1.5968 | C 58.08<br>H 4.22<br>N 4.52<br>Cl 22.86 | C 58.17<br>H 4.24<br>N 4.47<br>Cl 22.88 |
| 142 | I | (2,3-Cl₂)⟨⟩—O—⟨⟩—CON(C₃H₇(iso))H | M.P. 113–114° C. | C 59.27<br>H 4.66<br>N 4.32<br>Cl 21.87 | C 59.33<br>H 4.69<br>N 4.30<br>Cl 21.70 |
| 143 | I | (2,3-Cl₂)⟨⟩—O—⟨⟩—CON(C₄H₉(tert))H | M.P. 99–100.5° C. | C 60.36<br>H 5.07<br>N 4.14<br>Cl 20.97 | C 60.35<br>H 5.10<br>N 4.11<br>Cl 21.05 |
| 144 | I | (2,4-Cl₂)⟨⟩—O—⟨⟩—CON(C₂H₅)H | M.P. 49.5–51° C. | C 58.08<br>H 4.22<br>N 4.52<br>Cl 22.86 | C 58.14<br>H 4.19<br>N 4.48<br>Cl 22.93 |
| 145 | I | (2,4-Cl₂)⟨⟩—O—⟨⟩—CON(C₃H₇(iso))H | M.P. 102–103° C. | C 59.27<br>H 4.66<br>N 4.32<br>Cl 21.87 | C 59.32<br>H 4.63<br>N 4.35<br>Cl 21.91 |
| 146 | I | (2,4-Cl₂)⟨⟩—O—⟨⟩—CON(C₄H₉(tert))H | M.P. 108–109.5° C. | C 60.36<br>H 5.07<br>N 4.14<br>Cl 20.97 | C 60.25<br>H 5.07<br>N 4.11<br>Cl 20.99 |
| 147 | I | (2,5-Cl₂)⟨⟩—O—⟨⟩—CON(C₂H₅)H | M.P. 74.5–75.5° C. | C 58.08<br>H 4.22<br>N 4.52<br>Cl 22.86 | C 58.16<br>H 4.25<br>N 4.49<br>Cl 22.97 |
| 148 | I | (2,5-Cl₂)⟨⟩—O—⟨⟩—CON(C₃H₇(iso))H | M.P. 115–117° C. | C 59.27<br>H 4.66<br>N 4.32<br>Cl 21.87 | C 59.38<br>H 4.69<br>N 4.32<br>Cl 21.88 |

TABLE 1-continued

| Compound No. | Process | Compound | Physical property | Elementary analysis Calcd. (%) | Found (%) |
|---|---|---|---|---|---|
| 149 | I | 2,4-dichlorophenoxy, N-tert-butyl benzamide | M.P. 121–122° C. | C 60.36<br>H 5.07<br>N 4.14<br>Cl 20.97 | C 60.27<br>H 5.13<br>N 4.22<br>Cl 21.13 |
| 150 | I | 3,4-dichlorophenoxy, N-ethyl benzamide | M.P. 58.5–60° C. | C 58.08<br>H 4.22<br>N 4.52<br>Cl 22.86 | C 58.01<br>H 4.25<br>N 4.49<br>Cl 22.92 |
| 151 | I | 3,4-dichlorophenoxy, N-isopropyl benzamide | M.P. 73–74° C. | C 59.27<br>H 4.66<br>N 4.32<br>Cl 21.87 | C 59.25<br>H 4.69<br>N 4.30<br>Cl 21.96 |
| 152 | I | 3,4-dichlorophenoxy, N-tert-butyl benzamide | M.P. 112.5–114° C. | C 60.36<br>H 5.07<br>N 4.14<br>Cl 20.97 | C 60.36<br>H 5.05<br>N 4.13<br>Cl 21.02 |
| 153 | III | 3,5-dichlorophenoxy, N-ethyl benzamide | M.P. 139–141° C. | C 58.08<br>H 4.22<br>N 4.52<br>Cl 22.86 | C 58.00<br>H 4.23<br>N 4.55<br>Cl 22.90 |
| 154 | III | 3,5-dichlorophenoxy, N-isopropyl benzamide | M.P. 141.5–143° C. | C 59.27<br>H 4.66<br>N 4.32<br>Cl 21.87 | C 59.22<br>H 4.63<br>N 4.35<br>Cl 21.89 |
| 155 | III | 3,5-dichlorophenoxy, N-tert-butyl benzamide | M.P. 108.5–110° C. | C 60.36<br>H 5.07<br>N 4.14<br>Cl 20.97 | C 60.43<br>H 5.09<br>N 4.21<br>Cl 20.95 |
| 156 | II | 4-chloro-2-methylphenoxy, N-ethyl benzamide | $[\eta]_D^{24.5}$ 1.5747 | C 66.32<br>H 5.57<br>N 4.84<br>Cl 12.24 | C 66.27<br>C 5.53<br>N 4.80<br>Cl 12.20 |
| 157 | II | 4-chloro-2-methylphenoxy, N-isopropyl benzamide | M.P. 108–109° C. | C 67.21<br>H 5.97<br>N 4.61<br>Cl 11.67 | C 67.17<br>H 5.99<br>N 4.60<br>Cl 11.75 |
| 158 | II | 4-chloro-2-methylphenoxy, N-tert-butyl benzamide | M.P. 109.5–111° C. | C 68.02<br>H 6.34<br>N 4.41<br>Cl 11.61 | C 68.04<br>H 6.32<br>N 4.40<br>Cl 11.59 |
| 159 | I | 4-chloro-3-methylphenoxy, N-ethyl benzamide | M.P. 52.5–53.5° C. | C 66.32<br>H 5.57<br>N 4.84<br>Cl 12.24 | C 66.43<br>H 5.59<br>N 4.80<br>Cl 12.20 |

TABLE 1-continued
| Compound No. | Process | Compound | Physical property | Elementary analysis Calcd. (%) | Found (%) |
|---|---|---|---|---|---|
| 160 | I | 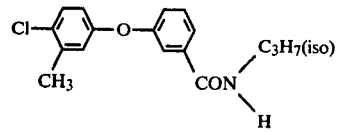 | M.P. 104.5–105.5° C. | C 67.21 H 5.97 N 4.61 Cl 11.67 | C 67.30 H 5.95 N 4.59 Cl 11.76 |
| 161 | I | 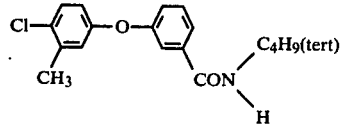 | M.P. 99–99.5° C. | C 68.02 H 6.34 N 4.41 Cl 11.61 | C 68.09 H 6.33 N 4.48 Cl 11.57 |
| 162 | I | 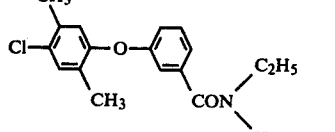 | M.P. 63–65° C. | C 67.21 H 5.97 N 4.61 Cl 11.67 | C 67.17 H 5.94 N 4.57 Cl 11.65 |
| 163 | I | 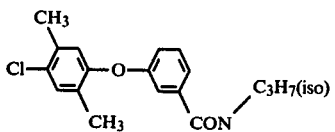 | M.P. 101–103.5° C. | C 68.02 H 6.34 N 4.41 Cl 11.16 | C 67.90 H 6.36 N 4.38 Cl 11.15 |
| 164 | I | 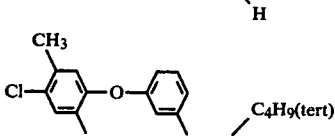 | M.P. 103.5–104.5° C. | C 68.77 H 6.68 N 4.22 Cl 10.69 | C 68.81 H 6.62 N 4.34 Cl 10.65 |
| 165 | II | 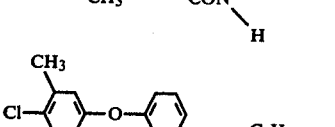 | $[\eta]_D^{23}$ 1.5850 | C 67.21 H 5.97 N 4.61 Cl 11.67 | C 67.19 H 5.99 N 4.60 Cl 11.70 |
| 166 | II | 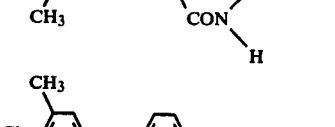 | M.P. 128.5–130° C. | C 68.02 H 6.34 N 4.41 Cl 11.16 | C 68.15 H 6.24 N 4.41 Cl 11.17 |
| 167 | II | 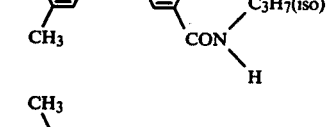 | M.P. 105.5–106.5° C. | C 68.77 H 6.68 N 4.22 Cl 10.69 | C 68.90 H 6.69 N 4.25 Cl 10.72 |
| 168 | I | 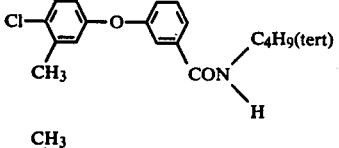 | $[\eta]_D^{23}$ 1.5863 | C 59.27 H 4.66 N 4.32 Cl 21.87 | C 59.30 H 4.68 N 4.30 Cl 21.79 |
| 169 | I | 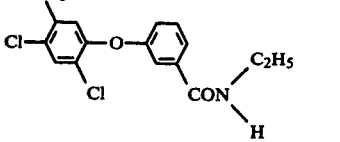 | $[\eta]_D^{23.5}$ 1.5823 | C 60.36 H 5.07 N 4.14 Cl 20.97 | C 60.43 H 5.09 N 4.12 Cl 21.20 |

TABLE 1-continued

| Compound No. | Process | Compound | Physical property | Elementary analysis Calcd. (%) | Found (%) |
|---|---|---|---|---|---|
| 170 | I | 4,5-dichloro-2-methylphenyl 3-(N-tert-butylcarbamoyl)phenyl ether | $[\eta]_D^{23.5}$ 1.5622 | C 61.37<br>H 5.44<br>N 3.98<br>Cl 20.13 | C 61.34<br>H 5.27<br>N 4.17<br>Cl 20.15 |
| 171 | I | 2-chloro-4-methylphenyl 3-(N-ethylcarbamoyl)phenyl ether | $[\eta]_D^{22.5}$ 1.5865 | C 66.32<br>H 5.57<br>N 4.84<br>Cl 12.24 | C 66.36<br>H 5.57<br>N 4.83<br>Cl 12.27 |
| 172 | I | 2-chloro-4-methylphenyl 3-(N-isopropylcarbamoyl)phenyl ether | M.P. 122–124° C. | C 67.21<br>H 5.97<br>N 4.61<br>Cl 11.67 | C 67.18<br>H 6.06<br>N 4.62<br>Cl 11.53 |
| 173 | I | 2-chloro-4-methylphenyl 3-(N-tert-butylcarbamoyl)phenyl ether | M.P. 86.5–88.5° C. | C 68.02<br>H 6.34<br>N 4.41<br>Cl 11.16 | C 68.10<br>H 6.31<br>N 4.44<br>Cl 11.19 |
| 174 | II | 3-chloro-5-methoxyphenyl 3-(N-ethylcarbamoyl)phenyl ether | M.P. 80.5–81.5° C. | C 62.84<br>H 5.28<br>N 4.58<br>Cl 11.60 | C 62.81<br>H 5.28<br>N 4.59<br>Cl 11.66 |
| 175 | II | 3-chloro-5-methoxyphenyl 3-(N-isopropylcarbamoyl)phenyl ether | M.P. 85–86.5° C. | C 63.85<br>H 5.67<br>N 4.38<br>Cl 11.09 | C 63.97<br>H 5.69<br>N 4.32<br>Cl 11.06 |
| 176 | II | 3-chloro-5-methoxyphenyl 3-(N-tert-butylcarbamoyl)phenyl ether | M.P. 85–86° C. | C 64.76<br>H 6.04<br>N 4.20<br>Cl 10.62 | C 64.79<br>H 6.07<br>N 4.22<br>Cl 10.63 |
| 177 | II | 4-chloro-3-methylphenyl 3-(N,N-diethylcarbamoyl)phenyl ether | $[\eta]_D^{23}$ 1.5682 | C 68.02<br>H 6.34<br>N 4.41<br>Cl 11.16 | C 67.98<br>H 6.37<br>N 4.43<br>Cl 11.20 |
| 178 | I | 4-chloro-3-methylphenyl 3-(N-isobutylcarbamoyl)phenyl ether | M.P. 79.5–80.5° C. | C 68.02<br>H 6.34<br>N 4.41<br>Cl 11.16 | C 67.16<br>H 6.31<br>N 4.45<br>Cl 11.28 |
| 179 | I | 4-chloro-3-methylphenyl 3-(N-benzylcarbamoyl)phenyl ether | M.P. 87.5–88° C. | C 71.69<br>H 5.16<br>N 3.98<br>Cl 10.08 | C 71.67<br>H 5.13<br>N 3.97<br>Cl 10.10 |
| 180 | I | 4-chloro-3-methylphenyl 3-(N-cyclopropylcarbamoyl)phenyl ether | M.P. 102–102.5° C. | C 67.66<br>H 5.34<br>N 4.64<br>Cl 11.75 | C 67.71<br>H 5.34<br>N 4.61<br>Cl 11.77 |

TABLE 1-continued

| Compound No. | Process | Compound | Physical property | Elementary analysis Calcd. (%) | Found (%) |
|---|---|---|---|---|---|
| 181 | I | 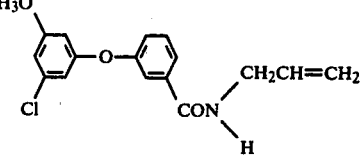 | $[\eta]_D^{27}$ 1.5916 | C 64.25<br>H 5.08<br>N 4.41<br>Cl 11.16 | C 64.14<br>H 5.11<br>N 4.40<br>Cl 11.29 |
| 182 | II | 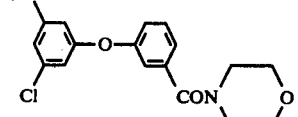 | $[\eta]_D^{21.5}$ 1.5947 | C 65.15<br>H 5.08<br>N 4.41<br>Cl 11.16 | C 65.00<br>H 5.47<br>N 4.26<br>Cl 10.73 |
| 183 | I | 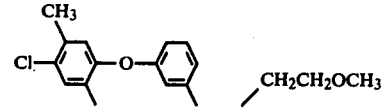 | M.P.<br>85.5–87° C. | C 64.76<br>H 6.04<br>N 4.20<br>Cl 10.62 | C 64.68<br>H 6.10<br>N 4.23<br>Cl 10.58 |
| 184 | I | 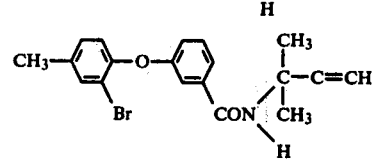 | M.P.<br>77–78° C. | C 61.30<br>H 4.87<br>N 3.76<br>Br 21.47 | C 61.35<br>H 4.84<br>N 3.77<br>Br 21.50 |
| 185 | I | 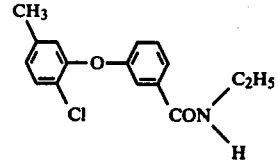 | $[\eta]_D^{23}$ 1.5778 | C 66.32<br>H 5.57<br>N 4.84<br>Cl 12.24 | C 66.34<br>H 5.55<br>N 4.83<br>Cl 12.17 |
| 186 | I | 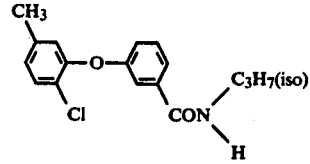 | M.P.<br>99–100° C. | C 67.21<br>H 5.97<br>N 4.61<br>Cl 11.67 | C 67.20<br>H 5.99<br>N 4.63<br>Cl 11.71 |
| 187 | I | 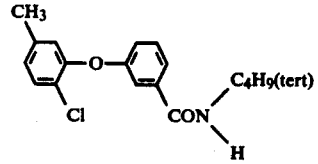 | M.P.<br>118.5–119.5° C. | C 68.02<br>H 6.34<br>N 4.41<br>Cl 11.16 | C 68.11<br>H 6.32<br>N 4.37<br>Cl 11.05 |
| 188 | I | 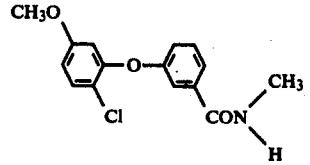 | M.P.<br>122–123.5° C. | C 61.75<br>H 4.84<br>N 4.80<br>Cl 12.16 | C 61.61<br>H 4.88<br>N 4.73<br>Cl 12.27 |
| 189 | I | 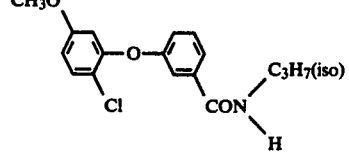 | M.P.<br>100–101° C. | C 63.85<br>H 5.67<br>N 4.38<br>Cl 11.09 | C 63.79<br>H 5.65<br>N 4.39<br>Cl 11.15 |
| 190 | I | 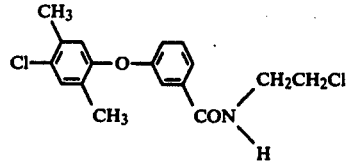 | $[\eta]_D^{22.5}$ 1.5722 | C 60.36<br>H 5.07<br>N 4.14<br>Cl 20.97 | C 60.35<br>H 5.06<br>N 4.18<br>Cl 20.89 |

TABLE 1-continued

| Compound No. | Process | Compound | Physical property | Elementary analysis Calcd. (%) | Elementary analysis Found (%) |
|---|---|---|---|---|---|
| 191 | III | F—⟨⟩—O—⟨⟩—CON(C$_2$H$_5$)(H) | B.P. 165–167° C./ 0.2 mmHg | C 69.48 H 5.44 N 5.40 | C 69.54 H 5.40 N 5.43 |
| 192 | I | Cl—⟨⟩(C$_2$H$_5$)—O—⟨⟩—CON(C$_3$H$_7$(iso))(H) | $[\eta]_D^{20.5}$ 1.5700 | C 68.02 H 6.34 N 4.41 Cl 11.16 | C 67.99 H 6.27 N 4.39 Cl 11.16 |
| 193 | III | F$_5$-phenyl—O—⟨⟩—CON(C$_3$H$_7$(iso))(H) | M.P. 118–119° C. | C 55.65 H 3.50 N 4.06 | C 55.48 H 3.44 N 4.25 |

When the m-phenoxybenzamide compounds (I) are used for practical purposes, they may be applied as such or in any preparation form of dusts, wettable powders, emulsifiable concentrates and the like.

These preparations are produced using a solid carrier or a liquid carrier. The solid carrier includes mineral powders (e.g. kaolin, bentonite, clay, montmorillonite, talc, diatomaceous earth, mica, vermiculite, slaked lime, calcium carbonate, apatite), vegetable powders (e.g. soybean powder, wheat powder, wooden powder, tobacco powder, starch, crystalline cellulose), polymers (e.g. petroleum resins, polyvinyl chloride resins, dammar gum, ketone resins), alumina, waxes and the like. The liquid carrier includes alcohols (e.g. methyl alcohol, ethyl alcohol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

The surface active agent used for emulsification, dispersion or spreading may be any of the nonionic, anionic, cationic and amphoteric agents. Examples of the surface active agent are polyoxyethylene alkyl ethers, polyoxyethylene alkylaryl ethers, polyoxyethylene fatty acid esters, sorbitan fatty acid esters, polyoxyethylene sorbitan fatty acid esters, oxyethylenes, oxypropylene polymers, polyoxy ethylene alkyl phosphates, fatty acid salts, salts of alkyl sulfates, alkyl sulfonates, alkylaryl sulfonates, salts of alkyl phosphates, polyoxyethylene alkyl sulfates, quaternary ammonium salts and the like.

In this case, auxiliary agents such as gelatin, casein, sodium alginate, starch, agar and polyvinyl alcohol may be used, if necessary.

The preparation examples of the herbicidal composition according to the present invention will be illustrated hereinafter.

PREPARATION EXAMPLE 1

Twenty-five parts by weight of the compound (4), 2.5 parts by weight of dodecyl benzenesulfonate, 2.5 parts by weight of a lignosulfonate and 70 parts by weight of diatomaceous earth were well mixed while being powdered. Thus, a wettable powder was obtained.

PREPARATION EXAMPLE 2

Thirty parts by weight of the compound (32), 10 parts by weight of an emulsifying agent ("Sorpol SM-100", registered trademark of Toho Kagaku Co., Ltd.) and 60 parts by weight of xylene were well mixed. Thus, an emulsifiable concentrate was obtained.

PREPARATION EXAMPLE 3

Five parts by weight of the compound (62), 1 part by weight of white carbon, 5 parts by weight of a lignosulfonate and 89 parts by weight of clay were well mixed while being powdered. The mixture was then well kneaded with water, granulated and dried to obtain a granule.

PREPARATION EXAMPLE 4

Three parts by weight of the compound (96), 1 part by weight of isopropyl phosphate, 66 parts by weight of clay and 30 parts by weight of talc were well mixed while being powdered. Thus, a dust was obtained.

PREPARATION EXAMPLE 5

Forty parts by weight of bentonite, 5 parts by weight of a lignosulfonate and 55 parts by weight of clay were well mixed while being powdered. The mixture was then kneaded with water, granulated and dried to obtain a granular product containing no active ingredient. Ninety-five parts by weight of this product was impregnated with 5 parts by weight of the compound (144). Thus, a granule was obtained.

PREPARATION EXAMPLE 6

Ninety-five parts by weight of bentonite passed through a 16 to 48 mesh sieve was impregnated with 5 parts by weight of the compound (156). Thus, a granule was obtained.

In the present invention, it is also possible to improve the herbicidal activity of the m-phenoxybenzamide compounds (I) by mixing them with other herbicides. Further, a synergistic effect may be expected in some cases.

As the herbicides which can be mixed with the m-phenoxybenzamide compounds (I), there may be exemplified phenoxy acid herbicides such as 2,4-dichlorophenoxyacetic acid and 2-methyl-4-chlorophenoxyacetic acid (including esters and salts thereof), diphenyl ether herbicides such as 2,4-dichlorophenyl-4'-nitrophenyl ether, 2,4,6-trichlorophenyl-4'-nitrophenyl ether, 3-methylphenyl-4'-nitrophenyl ether, 2,4-dichlorophenyl-4'-nitro-3'-methoxyphenyl ether and 2,4-dichlorophenyl-3'-methoxycarbonyl-4'-nitrophenyl ether, triazine herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine, 2-methylthio-4,6-bisisopropylamino-1,3,5-triazine and 2-methylthio-4-ethylamino-6-(1,2-dimethylpropyl)amino-1,3,5-triazine, urea herbicides such as 3-(3,4-dichlorophenyl)-1,1-dimethylurea, 3-(3,4-dichlorophenyl)-1-methoxy-1-methylurea, 3-(3-chloro-4-difluorochloromethylthiophenyl)-1,1-dimethylurea and 1-(2-phenylpropyl)-3-(4-methylphenyl)urea, carbamate herbicides such as isopropyl N-(3-chlorophenyl)carbamate and methyl N-(3,4-dichlorophenyl)carbamate, thiolcarbamate herbicides such as S-(4-chlorobenzyl)-N,N-diethylthiolcarbamate and S-ethyl-N,N-hexamethylenethiolcarbamate, acid anilide herbicides such as 3,4-dichloropropionanilide, N-methoxymethyl-2,6-diethyl-2-chloroacetanilide, 2-chloro-2',6'-diethyl-N-(butoxymethyl)acetanilide and N-chloroacetyl-N-(2,6-diethylphenyl)glycine ethyl ester, uracil herbicides such as 5-bromo-3-sec-butyl-6-methyluracil and 3-cyclohexyl-5,6-trimethylene uracil, pyridinium herbicides such as 1,1'-dimethyl-4,4'-bispyridinium dichloride, phosphorus herbicides such as N,N-bis(phosphonomethyl)glycine, O-ethyl-O-(2-nitro-5-methylphenyl)-N-sec-butylphosphoramidothioate, S-(2-methyl-1-piperidylcarbonylmethyl)-O,O-dipropylphosphorodithioate and O-methyl-O-(2-nitro-4-methylphenyl)N-isopropylphosphoramidothioate, toluidine herbicides such as α,α,α-trifluoro-2,6-dinitro-N,N-dipropyl-p-toluidine, 5-tert-butyl-3-(3,4-dichloro-5-isopropoxyphenyl)-1,3,4-oxadiazolin-2-one, 3-isopropyl-1H-2,1,3-benzothiadiazine-(4)-3H-one-2,2-dioxyd, α-(β-naphthoxy)propionanilide, 2-(α-naphthoxy)-N,N-diethylpropionamide, 3,3'-dimethyl-4-methoxybenzophenone and the like.

The herbicides of the invention may be used in combination with fungicides, microbial insecticides, pyrethroide type insecticides, other insecticides, plant regulators or fertilizers.

The present invention will be illustrated in more detail with reference to the following examples. The compounds used for the efficacy test are indicated by Compound No. in Table 1.

EXAMPLE A: PRE-EMERGENCE APPLICATION

The seeds of weeds such as large crabgrass (*Digitaria sanguinalis*), redroot pigweed (*Amaranthus retroflexus*) and common purslane (*Portulaca oleracea*) and those of crops such as soybean and sunflower were each sowed in a 10-cm flower pot and covered with soil. Separately from this, a required amount of each test compound was formulated into an emulsifiable concentrate and diluted with water. The diluted chemical solution was applied to the soil treatment by means of a hand sprayer. Each of the grasses and crops was grown up in a green-house, and the herbicidal activity and phytotoxicity of the test compound were checked 20 days after the application.

The test results are shown in Table 2. The herbicidal activity was evaluated in figures ranging from 0 to 5. The phytotoxicity to the crops was also indicated on the same standard as that of the herbicidal activity.

| Figures | Percentage of inhibition (%) |
|---------|------------------------------|
| 0 | 0 |
| 1 | 20 |
| 2 | 40 |
| 3 | 60 |
| 4 | 80 |
| 5 | 100 |

TABLE 2

| Compound No. | Amount applied (g/a) | Weeds Large crabgrass | Redroot pigweed | Common purslane | Crops Soybean | Sunflower |
|---|---|---|---|---|---|---|
| 1 | 40 | 5 | 5 | 5 | 0 | 0 |
|  | 20 | 5 | 5 | 5 | 0 | 0 |
| 2 | 40 | 5 | 5 | 5 | 0 | 0 |
|  | 20 | 5 | 5 | 5 | 0 | 0 |
| 3 | 40 | 5 | 5 | 5 | 0 | 0 |
|  | 20 | 5 | 5 | 5 | 0 | 0 |
| 5 | 40 | 5 | 5 | 5 | 0 | 0 |
|  | 20 | 5 | 5 | 5 | 0 | 0 |
| 6 | 40 | 5 | 5 | 5 | 0 | 0 |
|  | 20 | 5 | 5 | 5 | 0 | 0 |
| 8 | 80 | 5 | 5 | 5 | 0 | 0 |
|  | 40 | 5 | 5 | 5 | 0 | 0 |
| 9 | 40 | 5 | 5 | 5 | 0 | 0 |
|  | 20 | 5 | 5 | 5 | 0 | 0 |
| 12 | 80 | 5 | 5 | 5 | 0 | 0 |
|  | 40 | 4 | 4 | 5 | 0 | 0 |
| 14 | 40 | 5 | 5 | 5 | 0 | 0 |
|  | 20 | 5 | 5 | 5 | 0 | 0 |
| 16 | 40 | 5 | 5 | 5 | 0 | 0 |
|  | 20 | 5 | 5 | 5 | 0 | 0 |
| 17 | 40 | 5 | 5 | 5 | 0 | 0 |
|  | 20 | 5 | 5 | 5 | 0 | 0 |
| 18 | 80 | 5 | 5 | 5 | 0 | 0 |
|  | 40 | 5 | 5 | 5 | 0 | 0 |
| 20 | 80 | 5 | 5 | 5 | 0 | 0 |
|  | 40 | 4 | 5 | 5 | 0 | 0 |
| 22 | 80 | 5 | 5 | 5 | 0 | 0 |
|  | 40 | 4 | 4 | 5 | 0 | 0 |
| 23 | 80 | 5 | 5 | 5 | 0 | 0 |
|  | 40 | 5 | 5 | 5 | 0 | 0 |
| 26 | 40 | 5 | 5 | 5 | 0 | 0 |
|  | 20 | 5 | 5 | 5 | 0 | 0 |
| 27 | 80 | 5 | 5 | 5 | 0 | 0 |
|  | 40 | 5 | 5 | 5 | 0 | 0 |
| 30 | 40 | 5 | 5 | 5 | 0 | 0 |
|  | 20 | 5 | 5 | 5 | 0 | 0 |
| 31 | 80 | 5 | 5 | 5 | 0 | 0 |
|  | 40 | 4 | 4 | 4 | 0 | 0 |
| 33 | 40 | 5 | 5 | 5 | 0 | 0 |
|  | 20 | 5 | 5 | 5 | 0 | 0 |
| 34 | 40 | 5 | 5 | 5 | 0 | 0 |
|  | 20 | 5 | 5 | 5 | 0 | 0 |
| 36 | 40 | 5 | 5 | 5 | 0 | 0 |
|  | 20 | 5 | 5 | 5 | 0 | 0 |
| 38 | 40 | 5 | 5 | 5 | 0 | 0 |
|  | 20 | 5 | 5 | 5 | 0 | 0 |
| 40 | 40 | 5 | 5 | 5 | 0 | 0 |
|  | 20 | 5 | 5 | 5 | 0 | 0 |
| 41 | 40 | 5 | 5 | 5 | 0 | 0 |
|  | 20 | 5 | 5 | 5 | 0 | 0 |
| 43 | 40 | 5 | 5 | 5 | 0 | 0 |
|  | 20 | 5 | 5 | 5 | 0 | 0 |
| 44 | 40 | 5 | 5 | 5 | 0 | 0 |
|  | 20 | 5 | 5 | 5 | 0 | 0 |
| 47 | 40 | 5 | 5 | 5 | 0 | 0 |
|  | 20 | 5 | 5 | 5 | 0 | 0 |
| 49 | 40 | 5 | 5 | 5 | 0 | 0 |
|  | 20 | 5 | 5 | 5 | 0 | 0 |
| 51 | 40 | 5 | 5 | 5 | 0 | 0 |
|  | 20 | 5 | 5 | 5 | 0 | 0 |
| 53 | 40 | 5 | 5 | 5 | 0 | 0 |

TABLE 2-continued

| Compound No. | Amount applied (g/a) | Weeds | | | Crops | |
|---|---|---|---|---|---|---|
| | | Large crab-grass | Redroot pigweed | Common purslane | Soy-bean | Sun-flower |
| 54 | 20 | 5 | 5 | 5 | 0 | 0 |
| | 40 | 5 | 5 | 5 | 0 | 0 |
| 57 | 20 | 5 | 5 | 5 | 0 | 0 |
| | 40 | 5 | 5 | 5 | 0 | 0 |
| 58 | 80 | 5 | 5 | 5 | 0 | 0 |
| | 40 | 4 | 5 | 4 | 0 | 0 |
| 59 | 80 | 5 | 5 | 5 | 0 | 0 |
| | 40 | 5 | 5 | 5 | 0 | 0 |
| 61 | 40 | 5 | 5 | 5 | 0 | 0 |
| | 20 | 5 | 5 | 5 | 0 | 0 |
| 63 | 80 | 5 | 5 | 5 | 0 | 0 |
| | 40 | 5 | 5 | 5 | 0 | 0 |
| 64 | 40 | 5 | 5 | 5 | 0 | 0 |
| | 20 | 5 | 5 | 5 | 0 | 0 |
| 66 | 40 | 5 | 5 | 5 | 0 | 0 |
| | 20 | 5 | 5 | 5 | 0 | 0 |
| 67 | 40 | 5 | 5 | 5 | 0 | 0 |
| | 20 | 5 | 5 | 5 | 0 | 0 |
| 69 | 80 | 5 | 5 | 5 | 0 | 0 |
| | 40 | 5 | 5 | 5 | 0 | 0 |
| 71 | 40 | 5 | 5 | 5 | 0 | 0 |
| | 20 | 5 | 5 | 5 | 0 | 0 |
| 72 | 40 | 5 | 5 | 5 | 0 | 0 |
| | 20 | 5 | 5 | 5 | 0 | 0 |
| 74 | 40 | 5 | 5 | 5 | 0 | 0 |
| | 20 | 5 | 5 | 5 | 0 | 0 |
| 75 | 40 | 5 | 5 | 5 | 0 | 0 |
| | 20 | 5 | 5 | 5 | 0 | 0 |
| 76 | 40 | 5 | 5 | 5 | 0 | 0 |
| | 20 | 5 | 5 | 5 | 0 | 0 |
| 78 | 40 | 5 | 5 | 5 | 0 | 0 |
| | 20 | 5 | 5 | 5 | 0 | 0 |
| 79 | 40 | 5 | 5 | 5 | 0 | 0 |
| | 20 | 5 | 5 | 5 | 0 | 0 |
| 81 | 40 | 5 | 5 | 5 | 0 | 0 |
| | 20 | 5 | 5 | 5 | 0 | 0 |
| 83 | 40 | 5 | 5 | 5 | 0 | 0 |
| | 20 | 5 | 5 | 5 | 0 | 0 |
| 85 | 40 | 5 | 5 | 5 | 0 | 0 |
| | 20 | 5 | 5 | 5 | 0 | 0 |
| 86 | 40 | 5 | 5 | 5 | 0 | 0 |
| | 20 | 5 | 5 | 5 | 0 | 0 |
| 87 | 40 | 5 | 5 | 5 | 0 | 0 |
| | 20 | 5 | 5 | 5 | 0 | 0 |
| 90 | 80 | 5 | 5 | 5 | 0 | 0 |
| | 40 | 5 | 5 | 5 | 0 | 0 |
| 91 | 40 | 5 | 5 | 5 | 0 | 0 |
| | 20 | 5 | 5 | 5 | 0 | 0 |
| 92 | 40 | 5 | 5 | 5 | 0 | 0 |
| | 20 | 5 | 5 | 5 | 0 | 0 |
| 94 | 40 | 5 | 5 | 5 | 0 | 0 |
| | 20 | 5 | 5 | 5 | 0 | 0 |
| 96 | 40 | 5 | 5 | 5 | 0 | 0 |
| | 20 | 5 | 5 | 5 | 0 | 0 |
| 98 | 40 | 5 | 5 | 5 | 0 | 0 |
| | 20 | 5 | 5 | 5 | 0 | 0 |
| 99 | 40 | 5 | 5 | 5 | 0 | 0 |
| | 20 | 5 | 5 | 5 | 0 | 0 |
| 101 | 40 | 5 | 5 | 5 | 1 | 0 |
| | 20 | 5 | 5 | 5 | 0 | 0 |
| 102 | 40 | 5 | 5 | 5 | 0 | 0 |
| | 20 | 4 | 5 | 5 | 0 | 0 |
| 104 | 40 | 4 | 5 | 5 | 0 | 0 |
| | 20 | 4 | 4 | 5 | 0 | 0 |
| 105 | 40 | 4 | 5 | 5 | 0 | 0 |
| | 20 | 3 | 4 | 5 | 0 | 0 |
| 106 | 40 | 3 | 5 | 5 | 0 | 0 |
| | 20 | 2 | 4 | 5 | 0 | 0 |
| 108 | 40 | 5 | 5 | 5 | 0 | 0 |
| | 20 | 5 | 5 | 5 | 0 | 0 |
| 110 | 40 | 5 | 5 | 5 | 0 | 0 |
| | 20 | 3 | 5 | 5 | 0 | 0 |
| 111 | 40 | 5 | 5 | 5 | 1 | 0 |
| | 20 | 5 | 5 | 5 | 0 | 0 |
| 113 | 40 | 4 | 5 | 5 | 0 | 0 |
| | 20 | 3 | 4 | 5 | 0 | 0 |
| 114 | 80 | 5 | 5 | 5 | 0 | 0 |
| | 40 | 4 | 5 | 5 | 0 | 0 |
| 116 | 80 | 5 | 5 | 5 | 0 | 0 |
| | 40 | 4 | 5 | 5 | 0 | 0 |
| 117 | 40 | 4 | 5 | 5 | 0 | 0 |
| | 20 | 4 | 4 | 5 | 0 | 0 |
| 118 | 80 | 2 | 3 | 4 | 0 | 0 |
| | 40 | 1 | 2 | 3 | 0 | 0 |
| 121 | 40 | 5 | 5 | 5 | 0 | 0 |
| | 20 | 5 | 5 | 5 | 0 | 0 |
| 123 | 40 | 5 | 5 | 5 | 0 | 0 |
| | 20 | 5 | 5 | 5 | 0 | 0 |
| 124 | 40 | 5 | 5 | 5 | 0 | 0 |
| | 20 | 5 | 5 | 5 | 0 | 0 |
| 126 | 40 | 5 | 5 | 5 | 0 | 0 |
| | 20 | 5 | 5 | 5 | 0 | 0 |
| 127 | 40 | 5 | 5 | 5 | 0 | 0 |
| | 20 | 5 | 5 | 5 | 0 | 0 |
| 130 | 40 | 5 | 5 | 5 | 0 | 0 |
| | 20 | 5 | 5 | 5 | 0 | 0 |
| 131 | 40 | 5 | 5 | 5 | 0 | 0 |
| | 20 | 5 | 5 | 5 | 0 | 0 |
| 134 | 40 | 5 | 5 | 5 | 0 | 0 |
| | 20 | 5 | 5 | 5 | 0 | 0 |
| 135 | 40 | 5 | 5 | 5 | 0 | 0 |
| | 20 | 5 | 5 | 5 | 0 | 0 |
| 137 | 40 | 5 | 5 | 5 | 0 | 0 |
| | 20 | 5 | 5 | 5 | 0 | 0 |
| 138 | 40 | 5 | 5 | 5 | 0 | 0 |
| | 20 | 5 | 5 | 5 | 0 | 0 |
| 139 | 40 | 5 | 5 | 5 | 0 | 0 |
| | 20 | 5 | 5 | 5 | 0 | 0 |
| 141 | 40 | 5 | 5 | 5 | 0 | 0 |
| | 20 | 5 | 5 | 5 | 0 | 0 |
| 145 | 40 | 5 | 5 | 5 | 0 | 0 |
| | 20 | 5 | 5 | 5 | 0 | 0 |
| 148 | 40 | 5 | 5 | 5 | 0 | 0 |
| | 20 | 5 | 5 | 5 | 0 | 0 |
| 150 | 40 | 5 | 5 | 5 | 0 | 0 |
| | 20 | 5 | 5 | 5 | 0 | 0 |
| 151 | 40 | 5 | 5 | 5 | 0 | 0 |
| | 20 | 5 | 5 | 5 | 0 | 0 |
| 154 | 40 | 5 | 5 | 5 | 0 | 0 |
| | 20 | 5 | 5 | 5 | 0 | 0 |
| 156 | 40 | 5 | 5 | 5 | 0 | 0 |
| | 20 | 5 | 5 | 5 | 0 | 0 |
| 159 | 40 | 5 | 5 | 5 | 0 | 0 |
| | 20 | 5 | 5 | 5 | 0 | 0 |
| 162 | 40 | 5 | 5 | 5 | 0 | 0 |
| | 20 | 5 | 5 | 5 | 0 | 0 |
| 165 | 40 | 5 | 5 | 5 | 0 | 0 |
| | 20 | 5 | 5 | 5 | 0 | 0 |
| 168 | 40 | 5 | 5 | 5 | 0 | 0 |
| | 20 | 5 | 5 | 5 | 0 | 0 |
| 172 | 40 | 5 | 5 | 5 | 0 | 0 |
| | 20 | 5 | 5 | 5 | 0 | 0 |
| 174 | 40 | 5 | 5 | 5 | 0 | 0 |
| | 20 | 5 | 5 | 5 | 0 | 0 |
| 177 | 40 | 5 | 5 | 5 | 0 | 0 |
| | 20 | 5 | 5 | 5 | 0 | 0 |
| 191 | 40 | 5 | 5 | 5 | 0 | 0 |
| | 20 | 5 | 5 | 5 | 0 | 0 |
| 193 | 40 | 5 | 5 | 5 | 0 | 0 |
| | 20 | 5 | 5 | 5 | 0 | 0 |
| A*1 | 80 | 0 | 0 | 0 | 0 | 0 |
| | 40 | 0 | 0 | 0 | 0 | 0 |
| B*2 | 80 | 0 | 0 | 0 | 0 | 0 |
| | 40 | 0 | 0 | 0 | 0 | 0 |
| NIP*3 | 40 | 4 | 5 | 5 | 2 | 2 |
| | 20 | 4 | 4 | 5 | 1 | 0 |
| Cl- | 40 | 3 | 4 | 5 | 1 | 2 |

TABLE 2-continued

| Compound No. | Amount applied (g/a) | Weeds Large crab-grass | Redroot pigweed | Common purslane | Crops Soybean | Sunflower |
|---|---|---|---|---|---|---|
| IPC*4 | 20 | 2 | 1 | 4 | 1 | 1 |

Notes:
*1 Compound A: citation compound as disclosed in Zh.Org.Khim., 1968, 4 (10), 1836

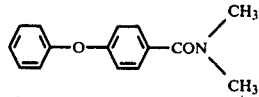

*2 Compound B: citation compound as disclosed in J. Karnatak Univ., 2.33 (1957)

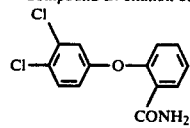

*3 NIP: commercial chemicals as control.

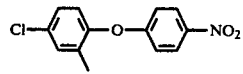

*4 Cl-IPC: commercial chemicals as control.

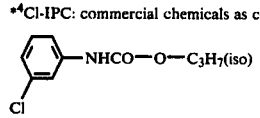

EXAMPLE B: FLOOD-WATER APPLICATION

A Wagner pot of 14 cm in diameter was filled with 1.5 kg of paddy field soil and brought into the state of a paddy field. Rice seedlings of the 3-leaf stage were transplanted in the pot, and seeds of barnyard grass (*Echinochloa crus-galli*) were further sowed therein. A required amount of each test compound was applied to the soil under a water-logged condition. Twenty-five days after the application, the herbicidal activity and phytotoxicity of the test compound were checked on the transplanted and sowed plants and spontaneously germinated broad-leaved weeds such as monochoria (*Monochoria viaginalis* Presl.), false pimpernel (*Linderna pyxidaria*) and toothcup (*Rotala indica* Koehne). The results are shown in Table 3.

As to the application, a wettable powder containing a required amount of the test compound was applied in a proportion of 15 ml/pot by means of a pipette. The herbicidal activity was evaluated in figures from 0 to 5.

| Figures | Percentage of inhibition (%) |
|---|---|
| 0 | 0 |
| 1 | 20 |
| 2 | 40 |
| 3 | 60 |
| 4 | 80 |
| 5 | 100 |

As to the evaluation of phytotoxicity, the three factors (i.e. height of plant, number of tillers and total weight (dry weight)) were each checked, and a ratio of the treated plot to the untreated plot was calculated for each factor. The phytotoxicity was evaluated based on the highest value of the three ratios which was classified into the following grades ranging from 0 to 5.

| Grade | Ratio of the untreated plot (%) |
|---|---|
| 0 | 100 |
| 1 | 80 |
| 2 | 60 |
| 3 | 40 |
| 4 | 20 |
| 5 | 0 |

TABLE 3

| Compound No. | Amount applied (g/a) | Herbicidal activity Barnyard grass | Broad-leaved grass | Phytotoxicity to plant |
|---|---|---|---|---|
| 4 | 20 | 5 | 5 | 0 |
|   | 10 | 5 | 5 | 0 |
| 7 | 20 | 5 | 5 | 0 |
|   | 10 | 5 | 5 | 0 |
| 10 | 20 | 5 | 5 | 0 |
|   | 10 | 5 | 5 | 0 |
| 11 | 40 | 5 | 5 | 0 |
|   | 20 | 5 | 5 | 0 |
| 13 | 20 | 5 | 5 | 0 |
|   | 10 | 5 | 5 | 0 |
| 15 | 20 | 5 | 5 | 0 |
|   | 10 | 5 | 5 | 0 |
| 19 | 40 | 5 | 5 | 0 |
|   | 20 | 5 | 5 | 0 |
| 21 | 80 | 5 | 5 | 0 |
|   | 40 | 5 | 5 | 0 |
| 24 | 40 | 5 | 5 | 0 |
|   | 20 | 5 | 5 | 0 |
| 25 | 80 | 5 | 5 | 0 |
|   | 40 | 5 | 5 | 0 |
| 28 | 80 | 5 | 5 | 0 |
|   | 40 | 5 | 5 | 0 |
| 29 | 80 | 5 | 5 | 0 |
|   | 40 | 5 | 5 | 0 |
| 32 | 40 | 5 | 5 | 0 |
|   | 20 | 5 | 5 | 0 |
| 33 | 20 | 5 | 5 | 0 |
|   | 10 | 5 | 5 | 0 |
| 35 | 20 | 5 | 5 | 0 |
|   | 10 | 5 | 5 | 0 |
| 37 | 20 | 5 | 5 | 0 |
|   | 10 | 5 | 5 | 0 |
| 39 | 20 | 5 | 5 | 0 |
|   | 10 | 5 | 5 | 0 |
| 42 | 20 | 5 | 5 | 0 |
|   | 10 | 5 | 5 | 0 |
| 45 | 20 | 5 | 5 | 0 |
|   | 10 | 5 | 5 | 0 |
| 46 | 80 | 5 | 5 | 0 |
|   | 40 | 5 | 5 | 0 |
| 48 | 20 | 5 | 5 | 0 |
|   | 10 | 5 | 5 | 0 |
| 50 | 20 | 5 | 5 | 0 |
|   | 10 | 5 | 5 | 0 |
| 52 | 20 | 5 | 5 | 0 |
|   | 10 | 5 | 5 | 0 |
| 55 | 20 | 5 | 5 | 0 |
|   | 10 | 5 | 5 | 0 |
| 56 | 20 | 5 | 5 | 0 |
|   | 10 | 5 | 5 | 0 |
| 60 | 20 | 5 | 5 | 0 |
|   | 10 | 5 | 5 | 0 |
| 61 | 20 | 5 | 5 | 0 |
|   | 10 | 5 | 5 | 0 |
| 62 | 20 | 5 | 5 | 0 |
|   | 10 | 5 | 5 | 0 |
| 65 | 20 | 5 | 5 | 0 |
|   | 10 | 5 | 5 | 0 |
| 68 | 40 | 5 | 5 | 0 |
|   | 20 | 5 | 5 | 0 |
| 70 | 40 | 5 | 5 | 0 |
|   | 20 | 5 | 5 | 0 |
| 73 | 40 | 5 | 5 | 0 |
|   | 20 | 5 | 5 | 0 |
| 75 | 20 | 5 | 5 | 0 |
|   | 10 | 5 | 5 | 0 |
| 77 | 20 | 5 | 5 | 0 |

TABLE 3-continued

| Compound No. | Amount applied (g/a) | Herbicidal activity Barnyard grass | Herbicidal activity Broad-leaved grass | Phytotoxicity to plant |
|---|---|---|---|---|
|  | 10 | 5 | 5 | 0 |
| 80 | 20 | 5 | 5 | 0 |
|  | 10 | 5 | 5 | 0 |
| 82 | 80 | 5 | 5 | 0 |
|  | 40 | 5 | 5 | 0 |
| 84 | 20 | 5 | 5 | 0 |
|  | 10 | 5 | 5 | 0 |
| 87 | 20 | 5 | 5 | 0 |
|  | 10 | 5 | 5 | 0 |
| 89 | 20 | 5 | 5 | 0 |
|  | 10 | 5 | 5 | 0 |
| 92 | 20 | 5 | 5 | 0 |
|  | 10 | 5 | 5 | 0 |
| 93 | 20 | 4 | 5 | 0 |
|  | 10 | 3 | 5 | 0 |
| 95 | 20 | 5 | 5 | 0 |
|  | 10 | 5 | 5 | 0 |
| 97 | 20 | 5 | 5 | 0 |
|  | 10 | 5 | 5 | 0 |
| 98 | 20 | 5 | 5 | 0 |
|  | 10 | 5 | 5 | 0 |
| 103 | 20 | 5 | 5 | 0 |
|  | 10 | 5 | 5 | 0 |
| 106 | 20 | 5 | 5 | 0 |
|  | 10 | 5 | 5 | 0 |
| 109 | 40 | 5 | 5 | 0 |
|  | 20 | 4 | 5 | 0 |
| 112 | 20 | 5 | 5 | 0 |
|  | 10 | 5 | 5 | 0 |
| 115 | 20 | 5 | 5 | 0 |
|  | 10 | 5 | 5 | 0 |
| 119 | 20 | 5 | 5 | 0 |
|  | 10 | 5 | 5 | 0 |
| 111 | 20 | 5 | 5 | 0 |
|  | 10 | 5 | 5 | 0 |
| 120 | 20 | 5 | 5 | 0 |
|  | 10 | 5 | 5 | 0 |
| 122 | 20 | 5 | 5 | 0 |
|  | 10 | 5 | 5 | 0 |
| 125 | 20 | 5 | 5 | 0 |
|  | 10 | 5 | 5 | 0 |
| 128 | 20 | 5 | 5 | 0 |
|  | 10 | 5 | 5 | 0 |
| 129 | 20 | 5 | 5 | 0 |
|  | 10 | 5 | 5 | 0 |
| 132 | 20 | 5 | 5 | 0 |
|  | 10 | 5 | 5 | 0 |
| 133 | 20 | 5 | 5 | 0 |
|  | 10 | 5 | 5 | 0 |
| 136 | 20 | 5 | 5 | 0 |
|  | 10 | 5 | 5 | 0 |
| 140 | 20 | 5 | 5 | 0 |
|  | 10 | 5 | 5 | 0 |
| 142 | 20 | 5 | 5 | 0 |
|  | 10 | 5 | 5 | 0 |
| 143 | 20 | 5 | 5 | 0 |
|  | 10 | 5 | 5 | 0 |
| 144 | 20 | 5 | 5 | 0 |
|  | 10 | 5 | 5 | 0 |
| 146 | 20 | 5 | 5 | 0 |
|  | 10 | 5 | 5 | 0 |
| 147 | 20 | 5 | 5 | 0 |
|  | 10 | 5 | 5 | 0 |
| 149 | 20 | 5 | 5 | 0 |
|  | 10 | 5 | 5 | 0 |
| 152 | 20 | 5 | 5 | 0 |
|  | 10 | 5 | 5 | 0 |
| 153 | 20 | 5 | 5 | 0 |
|  | 10 | 5 | 5 | 0 |
| 155 | 20 | 5 | 5 | 0 |
|  | 10 | 5 | 5 | 0 |
| 157 | 20 | 5 | 5 | 0 |
|  | 10 | 5 | 5 | 0 |
| 158 | 20 | 5 | 5 | 0 |
|  | 10 | 5 | 5 | 0 |
| 160 | 20 | 5 | 5 | 0 |
|  | 10 | 5 | 5 | 0 |
| 161 | 20 | 5 | 5 | 0 |
|  | 10 | 5 | 5 | 0 |
| 163 | 20 | 5 | 5 | 0 |
|  | 10 | 5 | 5 | 0 |
| 164 | 20 | 5 | 5 | 0 |
|  | 10 | 5 | 5 | 0 |
| 166 | 20 | 5 | 5 | 0 |
|  | 10 | 5 | 5 | 0 |
| 167 | 20 | 5 | 5 | 0 |
|  | 10 | 5 | 5 | 0 |
| 169 | 20 | 5 | 5 | 0 |
|  | 10 | 5 | 5 | 0 |
| 170 | 20 | 5 | 5 | 0 |
|  | 10 | 5 | 5 | 0 |
| 171 | 10 | 5 | 5 | 0 |
|  | 10 | 5 | 5 | 0 |
| 173 | 20 | 5 | 5 | 0 |
|  | 10 | 5 | 5 | 0 |
| 175 | 20 | 5 | 5 | 0 |
|  | 10 | 5 | 5 | 0 |
| 176 | 20 | 5 | 5 | 0 |
|  | 10 | 5 | 5 | 0 |
| 178 | 20 | 5 | 5 | 0 |
|  | 10 | 5 | 5 | 0 |
| 179 | 40 | 5 | 5 | 0 |
|  | 20 | 4 | 5 | 0 |
| 180 | 40 | 4 | 5 | 0 |
|  | 20 | 4 | 4 | 0 |
| 181 | 20 | 5 | 5 | 0 |
|  | 10 | 5 | 5 | 0 |
| 182 | 40 | 4 | 5 | 0 |
|  | 20 | 3 | 4 | 0 |
| 183 | 20 | 5 | 5 | 0 |
|  | 10 | 5 | 5 | 0 |
| 184 | 20 | 5 | 5 | 0 |
|  | 10 | 5 | 5 | 0 |
| 185 | 20 | 5 | 5 | 0 |
|  | 10 | 5 | 5 | 0 |
| 186 | 20 | 5 | 5 | 0 |
|  | 10 | 5 | 5 | 0 |
| 187 | 20 | 5 | 5 | 0 |
|  | 10 | 5 | 5 | 0 |
| 188 | 40 | 5 | 5 | 0 |
|  | 20 | 5 | 5 | 0 |
| 189 | 20 | 5 | 5 | 0 |
|  | 10 | 5 | 5 | 0 |
| 190 | 40 | 5 | 5 | 0 |
|  | 20 | 5 | 5 | 0 |
| 192 | 20 | 5 | 5 | 0 |
|  | 10 | 5 | 5 | 0 |
| C*1 | 80 | 0 | 2 | 0 |
|  | 40 | 0 | 1 | 0 |
| D*2 | 80 | 0 | 1 | 0 |
|  | 40 | 0 | 0 | 0 |
| NIP*3 | 40 | 5 | 5 | 3 |
|  | 20 | 5 | 5 | 2 |

Note: *1Compound C: citation compound as disclosed in Zh.Org.Khim., 1968, 4 (10), 1836

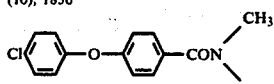

*2Compound D: citation compound as disclosed in J.Karnatak Univ., 3.63 (1958)

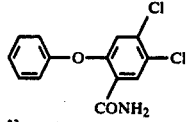

*3NIP: commercial chemicals as control.

EXAMPLE C: FLOOD-WATER APPLICATION (ON PERENNIAL WEEDS IN A PADDY FIELD)

A Wagner pot of 14 cm in diameter was filled with 1.5 kg of paddy field soil and brought into the state of a paddy field. The tuber of *Cyperus serotinus*, tuber of arrowhead sp. (*Sagittaria pygmaea*), seeds of hardstem bulrush (*Scirpus juncoides*) and overwintering bud of slender spikerush (*Eleocharis acicularis*) were each planted in the pot. A required amount of each test compound was applied to the soil under a water-logged condition. Twenty-five days after the application, the herbicidal activity on these weeds was checked. The results are shown in Table 4. The treating process and evaluation of herbicidal activity were carried out in the same manner as in Example B.

TABLE 4

| Compound No. | Amount applied (g/a) | Herbicidal activity | | | |
|---|---|---|---|---|---|
| | | Slender spikerush | Hardstem bulrush | Arrowhead sp. | Cyperus serotinus |
| 4 | 40 | 5 | 5 | 5 | 5 |
|   | 20 | 5 | 5 | 5 | 5 |
| 39 | 40 | 5 | 5 | 5 | 5 |
|    | 20 | 5 | 5 | 5 | 5 |
| 60 | 40 | 5 | 5 | 5 | 5 |
|    | 20 | 5 | 5 | 4 | 5 |
| 62 | 40 | 5 | 5 | 5 | 5 |
|    | 20 | 5 | 5 | 5 | 5 |
| 92 | 40 | 5 | 5 | 5 | 5 |
|    | 20 | 5 | 5 | 4 | 5 |
| 94 | 40 | 5 | 5 | 5 | 5 |
|    | 20 | 5 | 5 | 4 | 5 |
| 96 | 40 | 5 | 5 | 5 | 5 |
|    | 20 | 5 | 5 | 5 | 5 |
| 97 | 40 | 5 | 5 | 5 | 5 |
|    | 20 | 5 | 5 | 4 | 5 |
| 99 | 40 | 5 | 5 | 5 | 5 |
|    | 20 | 5 | 5 | 4 | 5 |
| 100 | 40 | 5 | 5 | 4 | 5 |
|     | 20 | 5 | 5 | 3 | 5 |
| 126 | 40 | 5 | 5 | 5 | 5 |
|     | 20 | 5 | 5 | 3 | 5 |
| 131 | 40 | 5 | 5 | 5 | 5 |
|     | 20 | 5 | 5 | 5 | 5 |
| 144 | 40 | 5 | 5 | 5 | 5 |
|     | 20 | 5 | 5 | 5 | 5 |
| 145 | 40 | 5 | 5 | 5 | 5 |
|     | 20 | 5 | 5 | 5 | 5 |
| 147 | 40 | 5 | 5 | 5 | 5 |
|     | 20 | 5 | 5 | 4 | 5 |
| 153 | 40 | 5 | 5 | 5 | 5 |
|     | 20 | 5 | 5 | 3 | 5 |
| 156 | 40 | 5 | 5 | 5 | 5 |
|     | 20 | 5 | 5 | 5 | 5 |
| 157 | 40 | 5 | 5 | 5 | 5 |
|     | 20 | 5 | 5 | 5 | 5 |
| 171 | 40 | 5 | 5 | 5 | 5 |
|     | 20 | 5 | 5 | 5 | 5 |
| 186 | 40 | 5 | 5 | 5 | 5 |
|     | 20 | 5 | 5 | 4 | 5 |
| A | 80 | 0 | 0 | 0 | 0 |
|   | 40 | 0 | 0 | 0 | 0 |
| B | 80 | 0 | 0 | 0 | 0 |
|   | 40 | 0 | 0 | 0 | 0 |
| NIP | 20 | 5 | 4 | 2 | 0 |
|     | 10 | 2 | 3 | 0 | 0 |

What is claimed is:

1. A herbicidal composition which comprises as an active ingredient a herbicidally effective amount of a m-phenoxybenzamide compound of the formula:

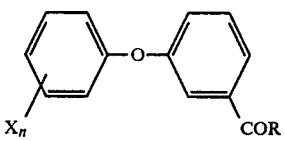

wherein X, which may be the same or different, is a halogen atom or a lower alkyl or lower alkoxy group, n is zero or an integer of 1 to 5 and R is a pyrrolidino or dimethylpyrrolidino group, and an inert carrier.

2. The herbicidal composition according to claim 1, wherein X, which may be the same or different, is a fluorine, chlorine or bromine atom or a $C_1$–$C_4$ alkyl or $C_1$–$C_3$ alkoxy group.

3. The herbicidal composition according to claim 1, wherein X, which may be the same or different, is a fluorine, chlorine or bromine atom, a methyl, ethyl or methoxy group, n is an integer of 1 to 3 and R is a pyrrolidino group.

4. The herbicidal composition according to claim 1 which has the preparation form of dust, wettable powder, solution, granule, fine granule, emulsifiable concentrate, oil or aerosol.

5. The herbicidal composition according to claim 1, further containing one or more active ingredients selected from the group consisting of insecticides, fungicides, nematocides, acaricides, herbicides and fertilizers.

6. A method for controlling the undesired growth of grasses or weeds which comprises applying an effective amount of a m-phenoxybenzamide compound of the formula:

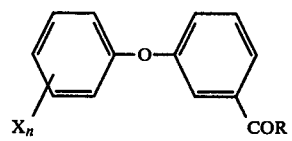

wherein X, which may be the same or different, is a halogen atom or a lower alkyl or lower alkoxy group, n is zero or an integer of 1 to 5 and R is a pyrrolidino or dimethylpyrrolidino group to the area where the control of the grasses or weeds is desired.

7. A m-phenoxybenzamide compound of the formula:

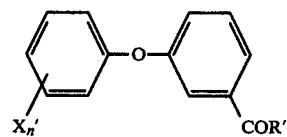

wherein X, which may be the same or different, is a halogen atom or a lower alkyl or lower alkoxy group, n' is zero or an integer of 1 to 5 and R' is a pyrrolidino or dimethylpyrrolidino group.

8. The m-phenoxybenzamide compound according to claim 7, wherein X, which may be the same or different, is a fluorine, chlorine or bromine atom or a $C_1$–$C_4$ alkyl or $C_1$–$C_3$ alkoxy group.

9. The m-phenoxybenzamide compound according to claim 7, wherein X, which may be the same or different, is a fluorine, chlorine or bromine atom or a methyl, ethyl or methoxy group and n' is an integer of 1 to 3.

* * * * *